US012721561B2

(12) United States Patent
Kim et al.

(10) Patent No.: US 12,721,561 B2
(45) Date of Patent: Sep. 1, 2026

(54) METHOD AND SYSTEM FOR PREDICTING BLADDER URINE VOLUME

(71) Applicant: MEDITHINGS CO., LTD., Seoul (KR)

(72) Inventors: Sehwan Kim, Seoul (KR); Aram Kim, Seoul (KR); Byeong-Il Kang, Seoul (KR); Jeonghun Kim, Seoul (KR)

(73) Assignee: MEDITHINGS CO., LTD., Seoul (KR)

( * ) Notice: Subject to any disclaimer, the term of this patent is extended or adjusted under 35 U.S.C. 154(b) by 0 days.

(21) Appl. No.: 18/944,532

(22) Filed: Nov. 12, 2024

(65) Prior Publication Data

US 2025/0152061 A1 May 15, 2025

(30) Foreign Application Priority Data

Nov. 13, 2023 (KR) ........................ 10-2023-0156772

(51) Int. Cl.
*A61B 5/20* (2006.01)
*A61B 5/00* (2006.01)

(52) U.S. Cl.
CPC ............ *A61B 5/204* (2013.01); *A61B 5/0082* (2013.01); *A61B 5/486* (2013.01); *A61B 5/6898* (2013.01);
(Continued)

(58) Field of Classification Search
CPC ........ A61B 5/204; A61B 5/0082; A61B 5/486; A61B 5/6898; A61B 5/7246; A61B 5/7267; A61B 5/7278; A61B 5/0059
See application file for complete search history.

(56) References Cited

U.S. PATENT DOCUMENTS

| | | | | |
|---|---|---|---|---|
| 8,221,337 B2 * | 7/2012 | Companion | ............. | A61B 8/08 340/573.5 |
| 12,446,813 B2 * | 10/2025 | Fallows | ................. | A61B 5/208 |

(Continued)

FOREIGN PATENT DOCUMENTS

| | | |
|---|---|---|
| CN | 114176526 A | 3/2022 |
| JP | 2011183142 A | 9/2011 |

(Continued)

OTHER PUBLICATIONS

Fechner [Near-Infrared Spectroscopy for Bladder Monitoring: A Machine Learning Approach, ACM Transactions on Management Information Systems, vol. 14, No. 2, Article 16. Publication date: Jan. 2023]. (Year: 2023).*

(Continued)

*Primary Examiner* — Oommen Jacob
(74) *Attorney, Agent, or Firm* — Banner & Witcoff, Ltd.

(57) ABSTRACT

The present disclosure provides a method and system for predicting a bladder urine volume. The method may include receiving an optical dataset associated with a specific user detected by a plurality of photodiodes, the plurality of photodiodes being configured to detect an intensity of light associated with light irradiated to skin located above the bladder of the specific user; estimating an optical characteristic value set for at least a part of the body of the specific user based on the optical dataset; and estimating a bladder urine volume of the specific user using a urine volume estimation model based on the estimated optical characteristic value set.

20 Claims, 17 Drawing Sheets

(52) U.S. Cl.
CPC .......... *A61B 5/7246* (2013.01); *A61B 5/7267* (2013.01); *A61B 5/7278* (2013.01)

(56) References Cited

U.S. PATENT DOCUMENTS

2005/0070816 A1 3/2005 Coats
2006/0100522 A1* 5/2006 Yuan .................... A61B 8/4483 600/466
2008/0294047 A1* 11/2008 Kodama .................. A61B 8/08 600/449
2010/0249664 A1* 9/2010 Burns .................. G01N 21/552 600/587
2015/0369725 A1* 12/2015 Carvalho Sousa .. A61B 5/1495 702/19
2018/0214122 A1* 8/2018 Ansell .................... G16H 50/20
2018/0289890 A1* 10/2018 Roth ....................... A61M 5/44
2019/0142324 A1* 5/2019 Papirov ................... G01F 23/00 600/407
2019/0150821 A1* 5/2019 Waters .................. A61B 5/1112
2019/0228867 A1 7/2019 Smyth et al.
2020/0022637 A1* 1/2020 Kurzrock ........... G01N 21/4738
2021/0121111 A1* 4/2021 Damaser ................ A61B 5/204
2025/0152061 A1* 5/2025 Kim ..................... A61B 5/6898

FOREIGN PATENT DOCUMENTS

KR 20200082673 A 7/2020
KR 102185227 B1 12/2020
KR 10-2021-0060800 A 5/2021
KR 102415948 B1 7/2022
KR 102415949 B1 7/2022
WO WO-2016025323 A1 * 2/2016 .............. A61M 5/00
WO WO-2018175100 A1 * 9/2018 ........... A61B 5/6823
WO 2019-104170 A2 5/2019
WO 2022182794 A1 9/2022

OTHER PUBLICATIONS

Farrell et al., "A diffusion theory model of spatially resolved, steady-state diffuse reflectance for the noninvasive determination of tissue optical properties in vivo", Med Phys. Jul.-Aug. 1992;19(4), pp. 879-888.
Mar. 19, 2025—(EP) Extended European Search Report—App. 24212429.5.
Mar. 21, 2025—(EP) Extended European Search Report—App 24213015.1.

* cited by examiner

METHOD AND SYSTEM FOR PREDICTING BLADDER URINE VOLUME

CROSS-REFERENCE TO RELATED APPLICATION

The present application claims priority to and the benefit of Korean Application No. 10-2023-0156772, filed on Nov. 13, 2023, in the Korean Intellectual Property Office, the entire disclosure of which is incorporated by reference herein.

BACKGROUND

1. Field

The present disclosure relates to a method and a system for predicting a bladder urine volume, and more particularly, to a method and a system for estimating physiological information based on optical information of a body.

2. Description of the Related Art

As we enter an aging society, one out of ten people aged 60 or older suffer from urinary disorders. In particular, patients with spinal cord injuries, dementia, stroke, urinary incontinence, or nocturia may find it difficult to independently judge the appropriate times for urination and/or catheterization. If urination and/or catheterization is not performed at the appropriate times, it may lead to mild bladder dysfunctions, such as frequent urination, urinary incontinence, and urinary retention, as well as complications like urinary tract infections, hydronephrosis, and vesicoureteral reflux.

For accurate diagnosis of urinary disorders, patients may visit a hospital and undergo tests, such as ultrasound bladder volume measurement or urodynamic studies, to assess bladder function by measuring the urine volume in the bladder. In other words, patients must visit the hospital and have their bladder volume measured by specialists through professional examinations to observe and diagnose bladder function.

Alternatively, patients with urinary disorders who experience unclear sensations of urine or incomplete urinary elimination need to perform urination and/or catheterization according to the guidelines provided by specialists after hospital diagnosis and/or according to set intervals given to the patient. Due to various factors such as the patient's daily physical condition or fluid intake, the patient's urine output may fall outside the normal range of typical urine output. In this case, relying on set intervals for urination and/or catheterization may lead to issues such as persistent urinary tract infections or decreased kidney function, due to failure to discharge urine at appropriate times. Therefore, following medical guidelines to perform urination and/or catheterization at regular intervals may lead to challenging issues for the patient, such as restrictions on outdoor activities or limitations on fluid intake.

SUMMARY

The present disclosure provides a method and a system (apparatus) for predicting a bladder urine volume to solve the above problems.

The present disclosure can be implemented in various ways, including a method, an apparatus (system), and/or a computer program stored in a computer-readable storage medium, and a computer-readable storage medium storing the computer program.

According to an aspect of the present disclosure, there is provided a bladder urine volume prediction method, performed by at least one processor, including: receiving an optical dataset associated with a specific user detected by a plurality of photodiodes, the plurality of photodiodes being configured to detect an intensity of light associated with light irradiated to skin located above the bladder of the specific user; estimating an optical characteristic value set for at least a part of the body of the specific user based on the optical dataset; and estimating a bladder urine volume of the specific user using a urine volume estimation model based on the estimated optical characteristic value set.

According to an aspect of the present disclosure, the urine volume estimation model may be a deep learning-based model or a machine learning-based model that has learned a plurality of learning datasets, and the plurality of learning datasets may include pairs of actual urine volumes of the specific user and optical characteristic value sets associated with the actual urine volumes.

According to an aspect of the present disclosure, the plurality of learning datasets may include a first learning dataset and a second learning dataset, the first learning dataset may include a pair of a first actual urine volume of the specific user and a first learning optical characteristic value set associated with the first actual urine volume.

According to an aspect of the present disclosure, the second learning dataset may include a pair of a second actual urine volume of the specific user and a second learning optical characteristic value set associated with the second actual urine volume.

According to an aspect of the present disclosure, the second actual urine volume may be greater than the first actual urine volume.

According to an aspect of the present disclosure, a teacher model may be generated by learning the plurality of learning datasets, the urine volume estimation model may further learn a single or a plurality of additional learning datasets, the additional learning datasets may include a pair of an additional learning urine volume and an additional learning optical characteristic value set estimated by inputting the additional learning urine volume into the teacher model, and the additional learning urine volume may be greater than the first urine volume and smaller than the second urine volume.

According to an aspect of the present disclosure, the urine volume estimation model may be learned by applying a predetermined weight to the plurality of learning datasets.

According to an aspect of the present disclosure, the first actual urine volume may correspond to a minimum bladder urine capacity of the specific user, and the second actual urine volume may correspond to the maximum bladder urine capacity of the specific user.

According to an aspect of the present disclosure, the method may further include outputting a message recommending voiding if the estimated urine volume information is greater than a predetermined reference value.

According to an aspect of the present disclosure, the urine volume estimation model may further learn learning obesity information, the method may further include: receiving obesity information associated with the specific user, and the estimating of the urine volume may include: estimating the urine volume using the urine volume estimation model based on the received obesity information and the optical characteristic value set.

According to an aspect of the present disclosure, there is provided a computer program stored in a computer-readable recording medium for executing the method according to an aspect of the present disclosure on a computer.

According to an aspect of the present disclosure, there is provided a user terminal including: a communication unit; a memory; and at least one processor connected to the memory and configured to execute at least one computer-readable program contained in the memory, the at least one program containing instructions for: receiving an optical dataset associated with a specific user detected by a plurality of photodiodes, the plurality of photodiodes being configured to detect an intensity of light associated with light irradiated to skin located above the bladder of the specific user; estimating an optical characteristic value set for at least a part of the body of the specific user based on the optical dataset; and estimating a bladder urine volume of the specific user using a urine volume estimation model based on the estimated optical characteristic value set.

According to some aspects of the present disclosure, physiological information can be provided to users without the assistance of a specialist such as a doctor. In addition, since the method of use is simple, it is possible to enhance the user convenience and increase the user's accessibility because it is personalized.

According to some aspects of the present disclosure, system parameters for a plurality of photodiodes included in-a medical device can be equally calibrated. Medical devices may not require additional calibration after generating one-time calibration parameters. In other words, calibration using a phantom is unnecessary, which can increase user convenience.

According to some aspects of the present disclosure, there is an advantage in that it can provide rapid calculations and high accuracy, thereby improving user convenience.

According to some aspects of the present disclosure, physiological information for a plurality of areas can be provided using a plurality of light sources and a plurality of photodiodes. Physiological information can be provided not only for a local area of the body but also for a wide area of the body. In addition, by providing physiological information for a plurality of areas, it is possible to specifically identify the state of an organ included in the body (for example, the urine volume stored in the bladder, the location of the bladder, and the like).

According to some aspects of the present disclosure, in the case of patients who do not feel the urge to urinate, physiological information about their bladder and/or the bladder urine volume can be provided in real-time or periodically. The patient can monitor the urine volume stored in their bladder through the provided information, and urinate at an appropriate time.

According to some aspects of the present disclosure, a urine volume estimation model can be provided in a customized manner to an individual user by learning the learning obesity information. In addition, since the urine volume estimation model uses a machine learning model or a deep learning model that is relatively well supported for application development, one or more aspects of the invention according to the present disclosure can facilitate the development of a mobile application for a wearable device. In addition, since the machine learning model or the deep learning model is easy to relearn, one or more aspects of the invention according to the present disclosure can realize personalized bladder urine volume estimation. In addition, the urine volume estimation model can be easily maintained and improved, and can have excellent model expandability and model universality.

According to some aspects of the present disclosure, when the amount of learning dataset is not large, data augmentation can be performed by generating a plurality of additional learning datasets through a teacher model. Since the urine volume prediction model learns more data through data augmentation, an automated bladder urine volume prediction method designed based on medical knowledge and diagnosis can be implemented.

The effects of the present disclosure are not limited to the effects described above, and other effects not described herein can be clearly understood by those of ordinary skill in the art (referred to as "ordinary technician") from the description of the claims.

BRIEF DESCRIPTION OF DRAWINGS

The above and other objects, features and advantages of the present disclosure will be described with reference to the accompanying drawings described below, where similar reference numerals indicate similar elements, but not limited thereto, in which.

DETAILED DESCRIPTION

Figure 1:
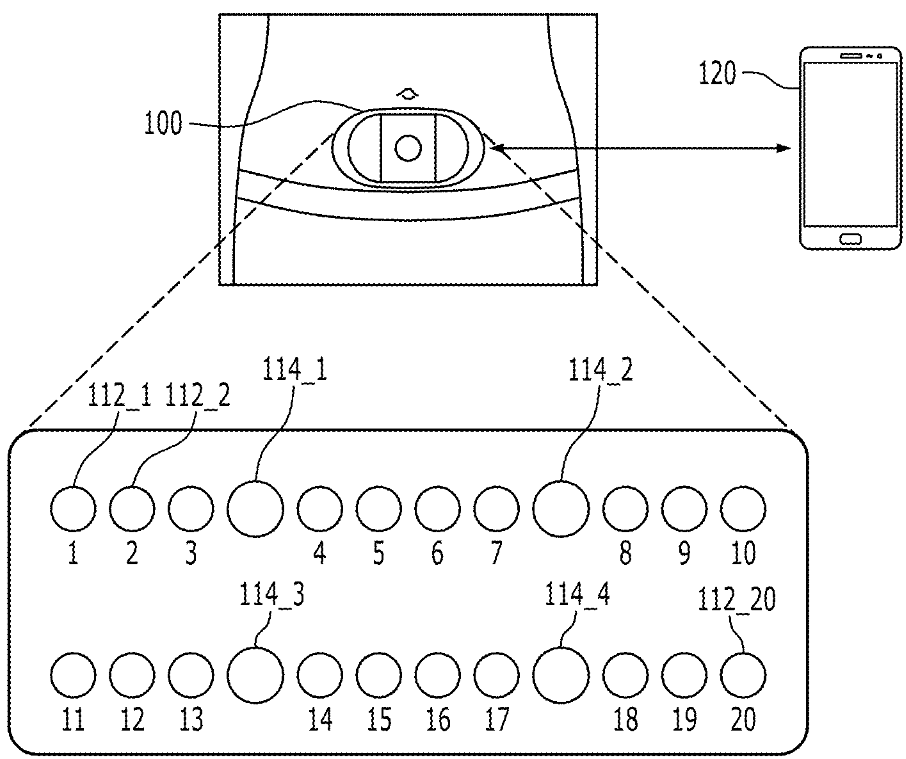
FIG. 1 is a schematic diagram illustrating an example of a medical device for estimating physiological information according to an aspect of the present disclosure.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it is intended as meaning that the portion may additionally comprise (or include or have) another component, rather than excluding the same, unless specified to the contrary.

Further, the term "module" or "part" used herein refers to a software or hardware component, and "module" or "part" performs certain roles. However, the meaning of the "module" or "part" is not limited to software or hardware. The "module" or "part" may be configured to be in an addressable storage medium or configured to play one or more processors. Accordingly, as an example, the "module" or "part" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "parts" may be combined into a smaller number of components and "modules" or "parts", or further divided into additional components and "modules" or "parts."

The "module" or "part" may be implemented as a processor and a memory. The "processor" should be interpreted broadly to encompass a general-purpose processor, a Central Processing Unit (CPU), a microprocessor, a Digital Signal Processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination for processing devices, for example, a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and the like. The memory is the to be in electronic communication with a processor if the processor can read information from and/or write information to the memory. The memory integrated with the processor is in electronic communication with the processor.

In addition, terms such as first, second, A, B, (a), (b), and the like used in the following description are only used to distinguish certain components from other components, and the nature, sequence, order, and the like of the components are not limited by the terms.

In addition, in the following description, if a certain component is stated as being "connected", "combined" or "coupled" to another component, it is to be understood that there may be yet another intervening component "connected", "combined" or "coupled" between the two components, although the two components may also be directly connected or coupled to each other.

In the present disclosure, "each of the plurality of A" may refer to each of all components included in the plurality of A, or may refer to each of some of the components included in a plurality of A.

In addition, as used in the following description, "comprise" and/or "comprising" does not foreclose the presence or addition of one or more other elements, steps, operations, and/or devices in addition to the recited elements, steps, operations, or devices.

In the present disclosure, "diffuse reflectance" may refer to the ratio of the light intensity of a light source to the light intensity of diffuse light measured at a specific distance from the light source. Here, diffuse light may refer to light diffused from an object irradiated with light. For example, when a body is irradiated with light, diffuse reflectance may refer to the ratio of the light intensity of a light source and the light intensity of diffuse light measured at a specific distance from the light source. Specifically, diffuse reflectance may be expressed as in Math. 1.

$$R = \frac{I_{out}}{I_{source}} \quad \text{[Math. 1]}$$

R means diffuse reflectance, $I_{out}$ means the light intensity of diffuse light measured at a specific distance from a light source, and $I_{source}$ means the light intensity of the light source.

In the present disclosure, "system parameter" may refer to a coefficient associated with light detection of a photodiode. The system parameter may include a proportional coefficient and an intercept coefficient. The proportional coefficient of the system parameter and the intercept coefficient of the system parameter may be understood through the description below.

If the optical data detected by the photodiode is a voltage value, it may be expressed as in Math. 2.

$$V = \alpha \times I + \beta \quad \text{[Math. 2]}$$

Here, V may represent the voltage value measured by the photodiode, and I may represent the light intensity of the diffuse light at a specific distance from the light source. In addition, a may represent the proportional coefficient of the system parameter, and β may represent the intercept coefficient of the system parameter. Here, the proportional coefficient of the system parameter may be a coefficient dependent on the photodiode and the wavelength of the light source. The intercept coefficient of the system parameter may be a coefficient dependent on the photodiode.

Hereinafter, various features of the present disclosure will be described in detail according to the attached drawings.

FIG. 1 is a schematic diagram illustrating an example of a medical device 100 for estimating physiological information according to an aspect of the present disclosure. As illustrated in the figure, the medical device 100 may include a communication unit to transmit and receive data to and from a user terminal 120. In addition, the medical device 100 may include a plurality of photodiodes 112_1 to 112_20 and a plurality of light source groups 114_1 to 114_4. The medical device 100 may obtain optical data associated with the body using the plurality of photodiodes 112_1 to 112_20 and the plurality of light source groups 114_1 to 114_4. The user terminal 120 may receive optical data associated with the body and estimate physiological information of the user based on the received optical data. Although FIG. 1 illustrates that the medical device 100 includes twenty photodiodes 112_1 to 112_20 and four light source groups 114_1 to 114_4, one or more aspects of the present invention is not limited thereto. That is, the number of photodiodes and the number of light source groups included in the medical device 100 may be changed as needed.

In an aspect, the plurality of photodiodes 112_1 to 112_20 and the plurality of light source groups 114_1 to 114_4 may be arranged on one surface of the medical device 100. In this case, the medical device 100 may be attached to the body so that the corresponding surface faces the body. In one example, the medical device 100 may be attached to the body so that the corresponding surface faces the area where the bladder is located.

In an aspect, each of the plurality of light source groups 114_1 to 114_4 may include six light sources having different wavelengths, but the present disclosure is not limited thereto. For example, the first light source group 114_1 may include the first to sixth light sources. The second light source group 114_2 may include the seventh to 12th light sources. The third light source group 114_3 may include the 13th to 18th light sources. The fourth light source group 114_4 may include the 19th to 24th light sources. Each of the first to 24th light sources may be an LD (Laser Diode), an LED (Light-Emitting Diode), or an OLED (Organic Light-Emitting Diode). In addition, each of the first to 24th light sources may emit continuous wave light.

In an aspect, the plurality of light sources included in each of the plurality of light source groups 114_1 to 114_4 may be configured to emit light of different wavelengths. For example, the first to sixth light sources included in the first light source group 114_1 may emit light of different wavelengths. In addition, the seventh to 12th light sources included in the second light source group 114_2 may emit light of different wavelengths. In addition, the 13th to 18th light sources included in the third light source group 114_3 may emit light of different wavelengths. In addition, the 19th to 24th light sources included in the fourth light source group 114_4 may emit light of different wavelengths.

Here, the light sources of different light source groups may emit light of the same wavelength. For example, the first, seventh, 13th, and 19th light sources may emit light of the same wavelength. Likewise, the second, eighth, 14th, and 20th light sources may emit light of the same wavelength. In addition, the third, ninth, 15th, and 21st light sources may emit light of the same wavelength. In addition, the fourth, 10th, 16th, and 22nd light sources may emit light of the same wavelength. In addition, the fifth, 11th, 17th, and 23rd light sources may emit light of the same wavelength. In addition, the sixth, 12th, 18th, and 24th light sources may emit light of the same wavelength.

In an aspect, the plurality of photodiodes 112_1 to 112_20 may detect light and generate optical data. Specifically, the plurality of photodiodes 112_1 to 112_20 may detect the light intensity of diffuse light, which is light diffused from a body. In addition, the plurality of photodiodes 112_1 to 112_20 may detect diffuse light associated with light sources emitted by light sources included in the plurality of light source groups 114_1 to 114_4. In addition, each photodiode may detect the diffuse light and measure a voltage value corresponding to the intensity of the diffuse light. At this time, one photodiode may detect the diffuse light in a state in which one light source is turned on.

In an aspect, the user terminal 120 may transmit an optical data detection request to the medical device 100. In response to the optical data detection request, the medical device 100 may perform the operation of the plurality of light source groups 114_1 to 114_4 and the detection of the plurality of photodiodes 112_1 to 112_20. The process for the operation of the plurality of light source groups 114_1 to 114_4 and the detection of the plurality of photodiodes 112_1 to 112_20 will be described in detail later with reference to FIG. 10. Alternatively, the medical device 100 may detect the optical data periodically and transmit it to the user terminal 120 without receiving the optical data detection request from the user terminal 120.

In an aspect, the medical device 100 may transmit a plurality of pieces of optical data detected through the plurality of photodiodes 112_1 to 112_20 to the user terminal 120. A processor included in the user terminal 120 may estimate physiological information based on the plurality of pieces of optical data. Here, the physiological information may include information on moisture ($H_2O$), information on fat, information on oxygenated hemoglobin ($HbO_2$), information on deoxygenated hemoglobin (HHb), bladder monitoring information (voiding time notification, Catheterization time notification, bladder urine volume, and the like). A method of estimating physiological information based on a plurality of pieces of optical data will be described in detail later with reference to FIGS. 4 to 12. In contrast, the medical device 100 may estimate physiological information directly based on the optical data without transmitting the optical data to the user terminal 120.

With this configuration, physiological information may be estimated based on the optical data obtained through the medical device 100. Additionally, the estimated physiological information may be provided to the user through the user terminal 120. In this way, according to the method according to the present disclosure, physiological information can be provided to users without the assistance of a specialist such as a doctor. In addition, according to the method according to the present disclosure, since the method of use is simple, it is possible to enhance the user convenience and increase the user's accessibility because it is personalized.

Figure 2:
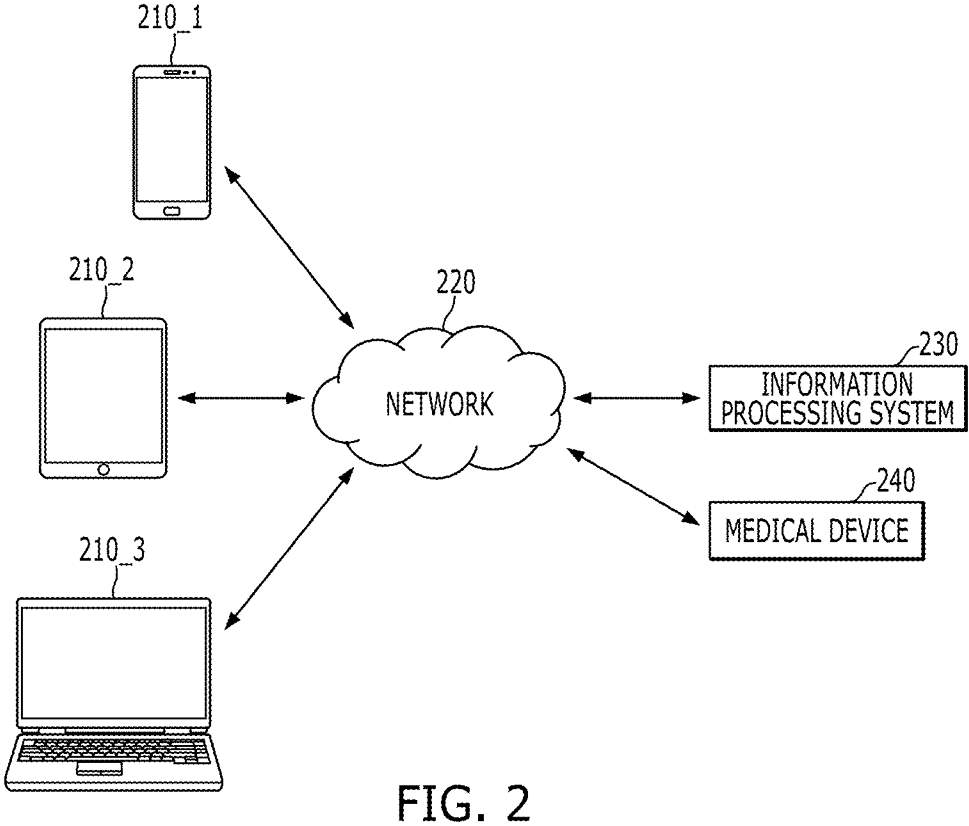
FIG. 2 is a schematic diagram illustrating a configuration of a configuration in which an information processing system, a medical device, and a plurality of user terminals according to an aspect of the present disclosure are communicably connected.

FIG. 2 is a schematic diagram illustrating a configuration in which an information processing system 230, a medical device 240, and a plurality of user terminals 210_1, 210_2, and 210_3 according to an aspect of the present disclosure are communicably connected. As illustrated in the figure, the plurality of user terminals 210_1, 210_2, and 210_3 may be connected to the information processing system 230 and the medical device 240 that may provide a physiological information estimation service and/or a digital voiding diary management service via a network 220. Here, the plurality of user terminals 210_1, 210_2 and 210_3 may include terminals of users who receive the physiological information estimation service.

According to an aspect, the information processing system 230 may include one or more server devices and/or databases capable of storing, providing, and executing computer-executable programs (for example, downloadable applications) and data associated with providing a physiological information estimation service, providing a digital voiding diary management service, and the like, or one or more distributed computing devices and/or distributed databases based on a cloud computing service.

The physiological information estimation service and/or digital voiding diary management service provided by the information processing system 230 may be provided to the user through a physiological information estimation service application or the like installed on each of the plurality of user terminals 210_1, 210_2, and 210_3. For example, the information processing system 230 may provide information associated with physiological information estimation and/or digital voiding diary management received from the user terminals 210_1, 210_2, and 210_3 and/or the medical device 240 through the physiological information estimation service application, the digital voiding diary management service application, and the like, or perform corresponding processing. In one example, the digital voiding diary management service provided by the information processing system 230 may also be accessed via the web. In addition, the digital voiding diary management service provided by the information processing system 230 may be accessed via PHR (Personal Health Record). It may be expanded to include EMR (Electronic Medical Record), EHR (Electronic Health Record), and the like.

According to an aspect, the information processing system 230 can estimate physiological information based on optical data. Here, the optical data may be data measured by the medical device 240. The information processing system 230 may directly receive optical data from the medical device 240 or may receive optical data through the user terminals 210_1, 210_2, and 210_3. The information processing system 230 may provide the physiological information estimation result to the user terminals 210_1, 210_2, and 210_3 and/or the medical device 240.

According to an aspect, the information processing system 230 may estimate the bladder urine volume for each of the plurality of time points based on a plurality of optical datasets. Here, the plurality of optical datasets may be data measured by the medical device 240. The information processing system 230 may receive a plurality of sets of optical data directly from the medical device 240 or may receive optical data through the user terminals 210_1, 210_2, and 210_3. In addition, the estimated bladder urine volume of a specific user for each of the plurality of time points may be recorded. At this time, the information processing system 230 may provide the recorded bladder urine volume of the specific user to the user terminals 210_1, 210_2, and 210_3 and/or the medical device 240.

The plurality of user terminals 210_1, 210_2, and 210_3 may communicate with the information processing system 230 and the medical device 240 through the network 220. The network 220 may be configured to enable communication between the plurality of user terminals 210_1, 210_2, and 210_3, the information processing system 230, and the medical device 240. Depending on the installation environment, the network 220 may be configured as, for example, a wired network such as Ethernet, a wired home network (Power Line Communication), a telephone line communication device, and RS-serial communication, a mobile communication network, a wireless LAN (WLAN), Wi-Fi, Bluetooth, and ZigBee, or a combination thereof. The communication method is not limited, and may include not only a communication method utilizing a communication network (for example, a mobile communication network, wired Internet, wireless Internet, a broadcasting network, a satellite network, and the like) that the network 220 may include, but also a short-range wireless communication between the user terminals 210_1, 210_2, and 210_3.

In FIG. 2, a mobile phone terminal 210_1, a tablet terminal 210_2, and a PC terminal 210_3 are illustrated as examples of user terminals, but are not limited thereto. The user terminals 210_1, 210_2, and 210_3 may be any computing device capable of wired and/or wireless communication and capable of installing and executing a physiological information estimation service application or a web browser. For example, the user terminal may include an AI speaker, a smartphone, a mobile phone, a navigation device, a computer, a laptop, a digital broadcasting terminal, a PDA (Personal Digital Assistants), a PMP (Portable Multimedia Player), a tablet PC, a game console, a wearable device, an IoT (Internet of Things) device, a VR (Virtual Reality) device, an AR (Augmented Reality) device, a set-top box, and the like. In addition, although FIG. 2 illustrates that three user terminals 210_1, 210_2, and 210_3 communicate with the information processing system 230 and the medical device 240 via the network 220, the present disclosure is not limited thereto. A different number of user terminals may be configured to communicate with the information processing system 230 and the medical device 240 via the network 220.

Figure 3:
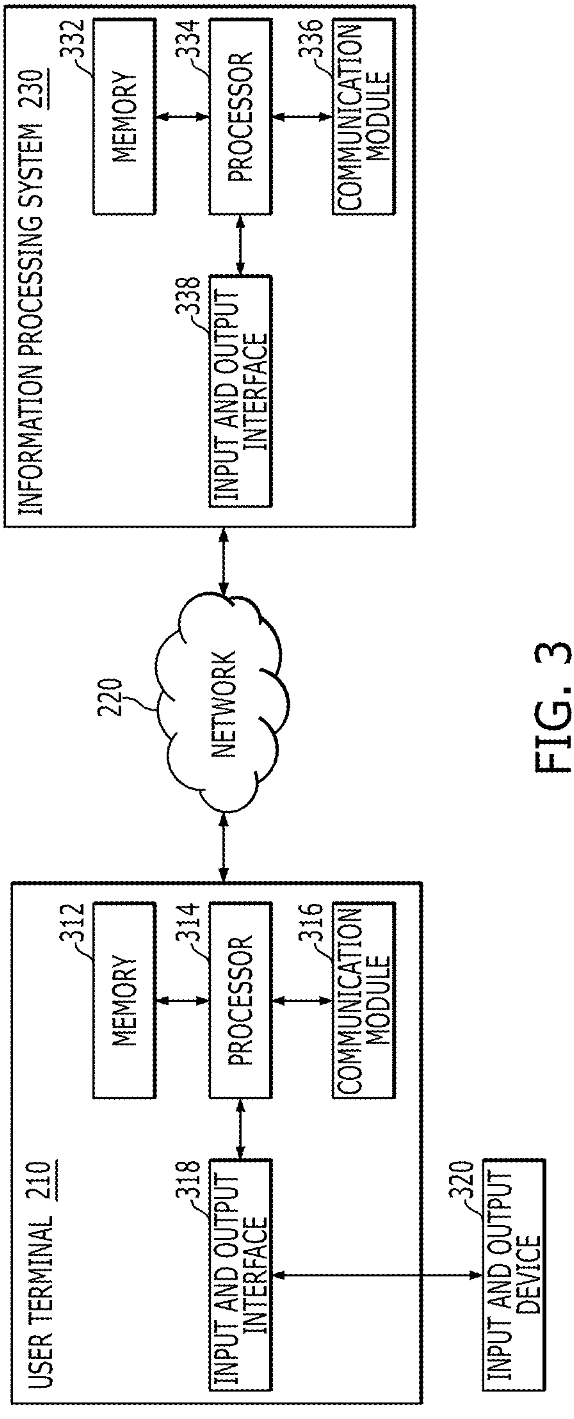
FIG. 3 is a block diagram illustrating an internal configuration of a user terminal and an information processing system according to an aspect of the present disclosure.

FIG. 3 is a block diagram illustrating the internal configuration of a user terminal and an information processing system according to an aspect of the present disclosure. The user terminal 210 may refer to any computing device capable of executing a physiological information estimation service application, a digital voiding diary management service application, and the like and capable of wired and wireless communication, and may include, for example, the mobile phone terminal 210_1, the tablet terminal 210_2, the PC terminal 210_3, and the like of FIG. 2. As illustrated in the figure, the user terminal 210 may include a memory 312, a processor 314, a communication module 316, and an input/output interface 318. Similarly, the information processing system 230 may include a memory 332, a processor 334, a communication module 336, and an input/output interface 338. As illustrated in FIG. 3, the user terminal 210 and the information processing system 230 may be configured to communicate information and/or data via the network 220 using the respective communication modules 316 and 336. In addition, the input/output device 320 may be configured to input information and/or data to the user terminal 210 or output information and/or data generated from the user terminal 210 via the input/output interface 318.

The memories 312 and 332 may include any non-transitory computer-readable recording medium. According to an aspect, the memories 312 and 332 may include a permanent mass storage device such as a read only memory (ROM), a disk drive, a solid state drive (SSD), a flash memory, and the like. As another example, the permanent mass storage device such as a ROM, an SSD, a flash memory, a disk drive, and the like may be included in the user terminal 210 or the information processing system 230 as a separate permanent storage device distinct from the memory. In addition, the memories 312 and 332 may store an operating system and at least one program code (for example, a code for a physiological information estimation service application installed and operated on the user terminal 210, a digital voiding diary management service application, and the like).

These software components may be loaded from a computer-readable recording medium separate from the memories 312 and 332. Such separate computer-readable recording media may include recording media directly connectable to the user terminal 210 and the information processing system 230, for example, computer-readable recording media such as floppy drives, disks, tapes, DVD/CD-ROM drives, memory cards, and the like. As another example, software components may be loaded into the memories 312 and 332 via a communication module other than a computer-readable recording medium. For example, at least one program may be loaded into the memories 312 and 332 based on a computer program that is installed by files provided by developers or a file distribution system that distributes installation files of applications via the network 220.

The processors 314 and 334 may be configured to process instructions of a computer program by performing basic arithmetic, logic, and input/output operations. Instructions may be provided to the processors 314 and 334 by the memories 312 and 332 or the communication modules 316 and 336. For example, the processors 314 and 334 may be configured to execute instructions received according to program code stored in a recording device such as the memories 312 and 332.

The communication modules 316 and 336 may provide a configuration or function for the user terminal 210 and the information processing system 230 to communicate with each other through the network 220, and may provide a configuration or function for the user terminal 210 and/or the information processing system 230 to communicate with another user terminal or another system (for example, a separate cloud system or the like). For example, a request or data (for example, optical data, a plurality of optical datasets, physiological information estimation request, a voiding diary, a voiding analysis result, and the like) generated by the processor 314 of the user terminal 210 according to a program code stored in a recording device such as the memory 312 may be transmitted to the information processing system 230 through the network 220 under the control of the communication module 316. Conversely, a control signal or command provided under the control of the processor 334 of, the information processing system 230 may be received by the user terminal 210 through the communication module 316 of the user terminal 210 via the communication module 336 and the network 220.

The input/output interface 318 may be a means for interfacing with the input/output device 320. For example, the input device may include a device such as a camera, a keyboard, a microphone, a mouse, and the like, including an audio sensor and/or an image sensor, and the output device may include a device such as a display, a speaker, a haptic feedback device, and the like. As another example, the input/output interface 318 may be a means for interfacing with a device that has an integrated configuration or function for performing input and output, such as a touchscreen. For example, when the processor 314 of the user terminal 210 processes a command of a computer program loaded into the memory 312, a service screen configured using information and/or data provided by the information processing system 230 or another user terminal may be displayed on the display through the input/output interface 318. Although the input/output device 320 is illustrated as not being included in the user terminal 210 in FIG. 3, the present disclosure is not limited thereto, and may be configured as a single device integrated with the user terminal 210. In addition, the input/output interface 338 of the information processing system 230 may be a means for interfacing with a device (not shown) for input or output that may be connected to the information processing system 230 or may be included in the information processing system 230. In FIG. 3, the input/output interfaces 318 and 338 are illustrated as an element configured separately from the processors 314 and 334, but the present disclosure is not limited thereto, and the input/output interfaces 318 and 338 may be configured to be included in the processors 314 and 334.

The user terminal 210 and the information processing system 230 may include more components than the components in FIG. 3. However, it is not necessary to clearly illustrate most of the conventional components. According to an aspect, the user terminal 210 may be implemented to include at least some of the above-described input/output devices 320. In addition, the user terminal 210 may further include other components such as a transceiver, a GPS (Global Positioning System) module, a camera, various sensors, a database, and the like. For example, if the user terminal 210 is a smartphone, it may include components that a smartphone generally includes. For example, the user terminal 210 may be implemented so as to further include various components such as an acceleration sensor, a gyro sensor, an image sensor, a proximity sensor, a touch sensor, an illuminance sensor, a camera module, various physical buttons, buttons using a touch panel, input/output ports, and a vibrator for vibration.

While the program for the physiological information estimation service application, the digital voiding diary management service application, and the like is running, the processor 314 may receive text, images, videos, voices, and/or actions, and the like input or selected through input devices such as a camera, microphone, and the like including a touch screen, keyboard, audio sensor, and/or image sensor connected to the input/output interface 318, and may store the received text, images, videos, voices, and/or actions, and the like in the memory 312 or provide them to the information processing system 230 through the communication module 316 and the network 220.

The processor 314 of the user terminal 210 may be configured to manage, process, and/or store information and/or data received from the input/output device 320, another user terminal, the information processing system 230, and/or a plurality of external systems. Information and/or data processed by the processor 314 may be provided to the information processing system 230 via the communication module 316 and the network 220. The processor 314 of the user terminal 210 may transmit information and/or data to the input/output device 320 via the input/output interface 318 and output the information and/or data. For example, the processor 314 may display the received information and/or data on the screen of the user terminal 210.

The processor 334 of the information processing system 230 may be configured to manage, process, and/or store the information and/or data received from the plurality of user terminals 210 and/or a plurality of external systems. The information and/or data processed by the processor 334 may be provided to the user terminal 210 via the communication module 336 and the network 220.

Figure 4:
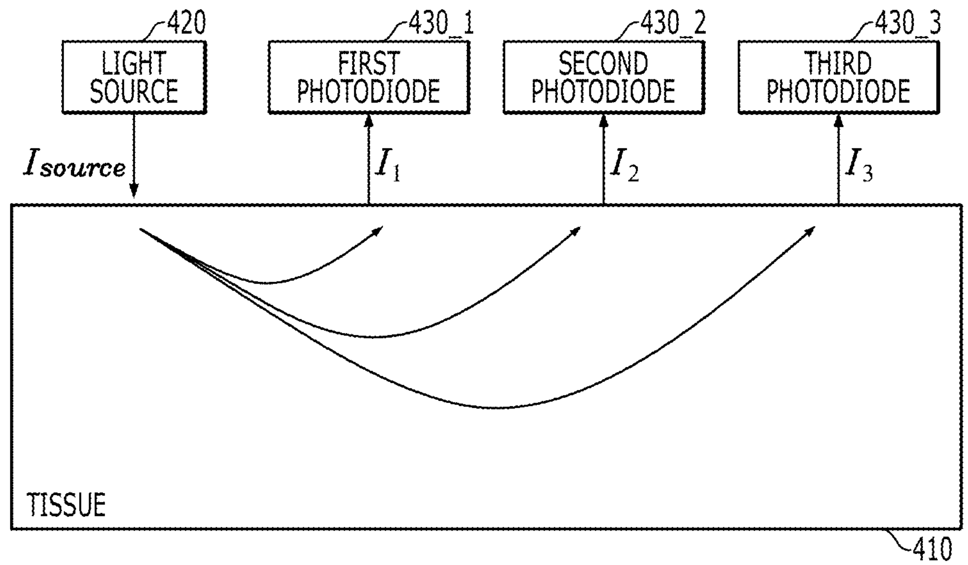
FIG. 4 is a diagram illustrating an example of detecting diffuse light using first to third photodiodes according to an aspect of the present disclosure.

FIG. 4 is a diagram illustrating an example of detecting diffuse light using the first to third photodiodes 430_1, 430_2, and 430_3 according to an aspect of the present disclosure. As illustrated in the figure, the light source 420 may emit light toward tissue 410, which is a part of the body. At this time, the intensity of the light emitted by the light source may be $I_{source}$. The first to third photodiodes 430_1, 430_2, and 430_3 may detect the diffuse light diffused by the tissue 410. At this time, the intensity of the diffuse light reaching the first photodiode may be $I_1$, the intensity of the diffuse light reaching the second photodiode may be $I_2$, and the intensity of the diffuse light reaching the third photodiode may be $I_3$. At this time, the first to third photodiodes 430_1, 430_2, and 430_3 may be at different distances from the light source.

In an aspect, the light source 420 may be one of the first to 24th light sources of the medical device 100 described in FIG. 1. The first to third photodiodes 430_1, 430_2, and 430_3 may be some of the plurality of photodiodes 112_1 to 112_20 of the medical device 100 described in FIG. 1. That is, the process of calculating the normalized diffuse reflectance based on the optical data detected by the plurality of photodiodes may be understood through the explanation of the examples of the light source 420, the first photodiode 430_1, the second photodiode 430_2, and the third photodiode 430_3.

In an aspect, the first to third photodiodes 430_1, 430_2, and 430_3 may detect the optical data. Specifically, the first to third photodiodes 430_1, 430_2, and 430_3 may measure the voltage value corresponding to the light intensity of the detected diffuse light. For example, the first photodiode 430_1 may measure $V_1$ as the voltage value corresponding to the diffuse light of $I_1$. In addition, the second photodiode 430_2 may measure $V_2$ as the voltage value corresponding to the diffuse light of $I_2$. In addition, the third photodiode 430_3 may measure $V_3$ as the voltage value corresponding to the diffuse light of $I_3$. Here, the plurality of measured voltage values may satisfy Math. 2. That is, using Math. 2, the diffuse reflectance $R_1$ of the first photodiode 430_1 may be $R_1=I_1/I_{source}$, the diffuse reflectance $R_2$ of the second photodiode 430_2 may be $R_2=I_2/I_{source}$, and the diffuse reflectance $R_3$ of the third photodiode 430_3 may be $R_3=I_3/I_{source}$.

In an aspect, the measured voltage value may be corrected using a calibration parameter. The corrected voltage value may be expressed as in Math. 3.

$$V_i' = (V_i - B_i') \times \alpha_i' = (\alpha_i \times I_i + B_i - B_i') \times \alpha_i' = \alpha_n \times I_i \qquad \text{[Math. 3]}$$

Here, $V_i'$ may represent a corrected voltage value of the i-th photodiode, $V_i$ may represent a measured voltage value (voltage value before correction) of the i-th photodiode, $\beta_i'$ may represent an intercept coefficient of the calibration parameter for the i-th photodiode, $\alpha_i'$ may represent a proportional coefficient of the calibration parameter for the i-th photodiode, $\alpha_i$ may represent a proportional coefficient of the system parameter for the i-th photodiode, $\alpha_i$ may represent an intercept coefficient of the system parameter for the i-th photodiode, and an may represent a corrected proportional coefficient. At this time, the corrected proportional coefficient may be the same for all of the plurality of photodiodes. In addition, the proportional coefficient of the calibration parameter may be $$a_i' = \alpha_n/\alpha_i,$$

and the intercept coefficient of the calibration parameter may be $$\beta_i' = \beta_i.$$

The method of generating the calibration parameter will be described in detail later with reference to FIGS. 6 to 8.

In an aspect, the system parameter may be different for each photodiode. Specifically, the proportional coefficient of the system parameter for each photodiode may be different from each other due to the influence of the error of the manufacturing process, the connected circuit device, and the like. As in Math. 3, the system parameter of each photodiode may be identically corrected using the calibration parameter.

The normalized diffuse reflectance may represent the relative relationship between the diffuse reflectance of a specific photodiode and the diffuse reflectance of another photodiode. Here, the normalized diffuse reflectance may be calculated based on the corrected voltage value. Specifically, the normalized diffuse reflectance may be understood through Math. 4 below. At this time, Math. 4 may be derived through Math. 1, Math. 2, and Math. 3.

$$R_{i/j} = \frac{R_i}{R_j} = \frac{I_i/I_{source}}{I_j/I_{source}} = \frac{I_i}{I_j} = \frac{V_i'}{V_j'} \times \frac{\alpha_n}{\alpha_n} = \frac{V_i'}{V_j'} \qquad \text{[Math. 4]}$$

Here, $R_{i/j}$ may represent the normalized diffuse reflectance, $R_i$ may represent the diffuse reflectance of the i-th photodiode, and $V_i'$ may represent the corrected measured voltage value of the i-th photodiode. In addition, $R_j$ may represent the diffuse reflectance of a specific photodiode that is a reference, and $V_j'$ may represent the corrected measured voltage value of a specific photodiode that is a reference. At this time, each photodiode may detect the light diffused from light having the same light intensity ($I_{source}$). That is, in Math. 4, $I_{source}$ may cancel each other. In addition, the corrected proportional coefficients of each photodiode may be the same. That is, in Math. 4, $\alpha_n$ may cancel each other. In this way, the normalized diffuse reflectance may be calculated based on the corrected voltage value.

According to the illustrated example, the first photodiode 430_1 may be located closest to the light source 420. The first photodiode 430_1 closest to the light source 420 may be selected as a reference for calculating the normalized diffuse reflectance. In this case, the normalized diffuse reflectance $R_2$n of the second photodiode 430_2 may be $R_{21}=V_2'N_1'$. Similarly, the normalized diffuse reflectance $R_{3/1}$ of the third photodiode 430_3 may be $R_{3/1}=V_3'/V_1'$.

In FIG. 4, the process of calculating the normalized diffuse reflectance associated with the light source 420 and the first to third photodiodes 430_1, 430_2, and 430_3 is described in detail. A method of estimating physiological information based on normalized diffuse reflectance associated with the light source 420 and the first to third photodiodes 430_1, 430_2, and 430_3 will be described in detail with reference to FIG. 5.

Figure 5:
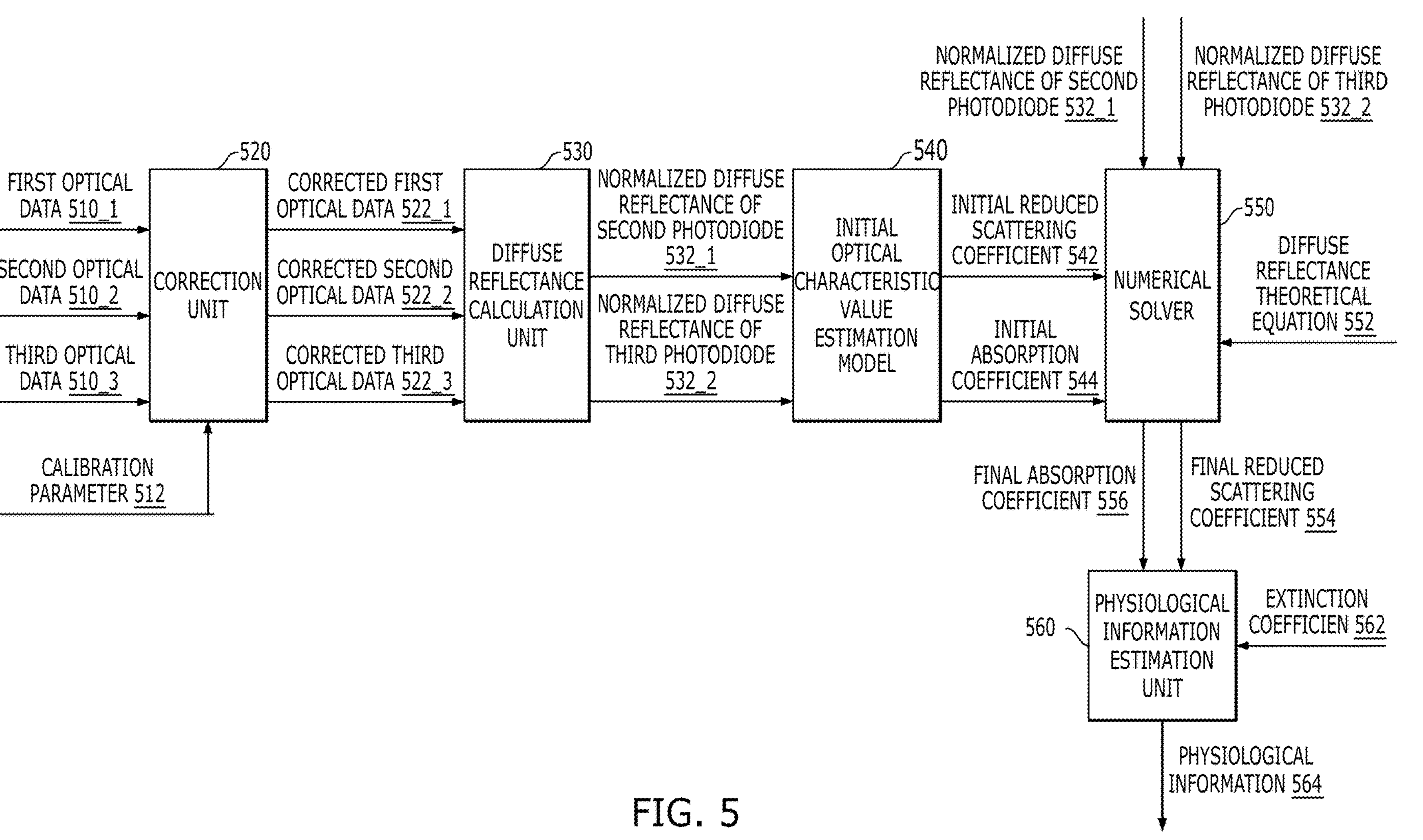
FIG. 5 is a diagram illustrating an example of a process for estimating physiological information according to an aspect of the present disclosure.

FIG. 5 is a diagram illustrating an example of a process for estimating physiological information according to an aspect of the present disclosure. The first optical data 510_1 may be data generated by the first photodiode. The second optical data 510_2 may be data generated by the second photodiode. The third optical data 510_3 may be data generated by the third photodiode. When measuring a voltage value corresponding to the intensity of light detected by each photodiode, the plurality of pieces of optical data 510_1, 510_2, and 510_3 may be measured voltage values. For example, the first optical data 510_1 may be the measured voltage value of the first photodiode described above in FIG. 4. Similarly, the second optical data 510_2 may be the measured voltage value of the second photodiode described above in FIG. 4. In addition, the third optical data 510_3 may be the measured voltage value of the third photodiode described above in FIG. 4.

In an aspect, the correction unit 520 may use the calibration parameter 512 based on the plurality of pieces of optical data 510_1, 510_2, and 510_3 to calculate the plurality of pieces of corrected optical data 522_1, 522_2, and 522_3. Specifically, each of the plurality of pieces of optical data 510_1, 510_2, and 510_3 may be corrected, and each of the plurality of pieces of corrected optical data 522_1, 522_2, and 522_3 may be calculated. For example, the corrected first optical data 522_1 may be the corrected voltage value of the first photodiode described above in FIG. 4. Similarly, the corrected second optical data 522_2 may be the corrected voltage value of the second photodiode described above in FIG. 4. In addition, the corrected third optical data 522_3 may be the corrected voltage value of the third photodiode described above in FIG. 4. The process of correcting the optical data using the calibration parameter 512 may be understood through the contents described above in FIG. 4.

In an aspect, the diffuse reflectance calculation unit 530 may calculate a plurality of normalized diffuse reflectances 532_1 and 532_2 based on the plurality of pieces of corrected optical data 522_1, 522_2, and 522_3. For example, the normalized diffuse reflectance 532_1 of the second photodiode may be calculated based on the corrected first optical data 522_1 and the corrected second optical data 522_2. Similarly, the normalized diffuse reflectance 532_2 of the third photodiode may be calculated based on the corrected first optical data 522_1 and the corrected third optical data 522_3. The process of calculating the normalized diffuse reflectance may be understood through the contents described above in FIG. 4.

In an aspect, the absorption coefficient and the reduced scattering coefficient may be estimated based on a plurality of normalized diffuse reflectances 532_1 and 532_2. Here, the absorption coefficient may be an optical coefficient of a biological tissue for analyzing a physiological component of a biological tissue according to the degree of light absorption for each wavelength in the biological tissue. In addition, the reduced scattering coefficient may be an optical coefficient representing structural characteristics of a biological tissue. For example, adipose tissue of an obese patient with large fat cells may have relatively little light scattering, and adipose tissue of a normal weight patient with small fat cells may have relatively good light scattering. As illustrated in the figure, an initial optical characteristic value estimation model 540 and/or a numerical solver 550 may be used to estimate the absorption coefficient and the reduced scattering coefficient.

In an aspect, the initial optical characteristic value estimation model 540 may estimate the initial optical characteristic value for a specific area based on a plurality of normalized diffuse reflectances 532_1 and 532_2. Here, the specific area may be a body part associated with the second photodiode and the third photodiode. The initial optical characteristic value may include an initial reduced scattering coefficient 542 and an initial absorption coefficient 544. For example, the initial optical characteristic value estimation model 540 may be an artificial neural network model (for example, a deep learning-based model) that has learned a plurality of optical characteristic values and a normalized theoretical diffuse reflectance associated with the plurality of optical characteristic values. The learning process of the initial optical characteristic value estimation model 540 will be described in detail with reference to FIG. 9.

In an aspect, a numerical solver 550 may estimate the final optical characteristic value based on the initial optical characteristic value. At this time, the final optical characteristic value may include the final reduced scattering coefficient 554 and the final absorption coefficient 556. In one example, the numerical solver 550 may use the Levenberg-Marquardt algorithm. Specifically, the numerical solver 550 may receive the initial optical characteristic value and a plurality of normalized diffuse reflectances 532_1 and 532_2 as initial values, and estimate the final optical characteristic value based on the diffuse reflectance theoretical equation 552.

Here, the diffuse reflectance theoretical equation 552 is as shown in Math. 5.

[Math. 5]

$$R(\rho) = \frac{1}{4\pi}\left[z_0\left(\mu_{eff} + \frac{1}{r_1}\right)\frac{e^{-\mu_{eff} r_1}}{r_1^2} + (z_0 + 2z_b)\left(\mu_{eff} + \frac{1}{r_2}\right)\frac{e^{-\mu_{eff} r_2}}{r_2^2}\right]$$

Here, R(φ may represent the theoretical diffuse reflectance, ρ may represent the distance between the light source and the photodiode, $\mu_\alpha$ may represent the absorption coefficient, and $$\mu_s'$$

may represent the reduced scattering coefficient. In addition, $$\mu_t'$$

may represent $$\mu_{eff} = [3\mu_\alpha(\mu_\alpha + \mu_s')]^{1/2}.$$

and $\mu_{eff}$ may represent the effective attenuation coefficient, which may be $$\mu_t' = \mu_s' + \mu_\alpha,$$

$z_b$ may be the core of the extrapolate boundary condition, and may be the value of the virtual boundary where the flux of the photon disappears. $z_b$ may be a value that may be theoretically calculated in response to the light source. Also, $$r_1 = \left[z_0^2 + \rho^2\right]^{1/2},$$

$r_2=[(z_0+2z_b)^{2+\rho 2}]^{1/2}$, Here $z_0$ may be $$z_0 = \mu_t'^{-1}.$$

Math. 5 may be understood as an equation for $\mu_\alpha$, $$\mu_s',$$

and $\rho$.

In an aspect, the numerical solver 550 may receive initial optical characteristic values and a plurality of normalized diffuse reflectances 532_1 and 532_2 for a specific area as initial values, and estimate the final optical characteristic values for the specific area based on the diffuse reflectance theoretical equation 552. Specifically, the initial reduced scattering coefficient 542 for a specific area, the initial absorption coefficient 544 for a specific area, the normalized diffuse reflectance 532_1 of the second photodiode, and the normalized diffuse reflectance 532_2 of the third photodiode are input as a set into the numerical solver 550, and the final reduced scattering coefficient 554 for a specific area and the final absorption coefficient 556 for a specific area may be estimated.

In an aspect, a physiological information estimation unit 560 may estimate the physiological information 564 of a specific area based on the final optical characteristic value. Specifically, the physiological information 564 may be estimated based on the extinction coefficient 562, the final reduced scattering coefficient 554, and the final absorption coefficient 556. For example, the extinction coefficient 562 may be expressed as an extinction coefficient matrix as shown in Table 1 below.

TABLE 1

| | | | | | |
|---|---|---|---|---|---|
| $\epsilon_{HbO2,\lambda 1}$ | $\epsilon_{HbO2,\lambda 2}$ | $\epsilon_{HbO2,\lambda 3}$ | $\epsilon_{HbO2,\lambda 4}$ | $\epsilon_{HbO2,\lambda 5}$ | $\epsilon_{HbO2,\lambda 6}$ |
| $\epsilon_{HHb,\lambda 1}$ | $\epsilon_{HHb,\lambda 2}$ | $\epsilon_{HHb,\lambda 3}$ | $\epsilon_{HHb,\lambda 4}$ | $\epsilon_{HHb,\lambda 5}$ | $\epsilon_{HHb,\lambda 6}$ |
| $\epsilon_{H2O,\lambda 1}$ | $\epsilon_{H2O,\lambda 2}$ | $\epsilon_{H2O,\lambda 3}$ | $\epsilon_{H2O,\lambda 4}$ | $\epsilon_{H2O,\lambda 5}$ | $\epsilon_{H2O,\lambda 6}$ |

$\epsilon_{HbO2,\lambda i}$ may be the extinction coefficient of oxygenated hemoglobin for the i-th wavelength, $\epsilon_{HHb,\lambda i}$ may be the extinction coefficient of deoxygenated hemoglobin for the i-th wavelength, $\epsilon_{H2O,\lambda i}$ may be the extinction coefficient of moisture for the i-th wavelength, and $\epsilon_{Fat,\lambda i}$ may be the extinction coefficient of fat for the i-th wavelength. Here, the extinction coefficient matrix may be a 4×6 matrix, but the present disclosure is not limited thereto. For example, the size of the extinction coefficient matrix may be changed according to the number of photodiodes, the number of light sources, and the like.

In an aspect, a pseudo inverse matrix of the extinction coefficient matrix as shown in Table 1 may be calculated. The physiological information 564 may be derived based on the wavelength-specific absorption coefficient using the inverse matrix of the absorption coefficient matrix. Specifically, the process of calculating physiological information through Math. 6, which multiplies the wavelength-specific absorption coefficient and the inverse matrix of the absorption coefficient matrix, will be examined.

$$\left[\mu_{a,\lambda_1}, \mu_{a,\lambda_2}, \mu_{a,\lambda_3}, \mu_{a,\lambda_4}, \mu_{a,\lambda_5}, \mu_{a,\lambda_6}\right] \cdot \begin{bmatrix} \epsilon'_{HbO_2,\lambda_1} & \epsilon'_{HHb,\lambda_1} & \epsilon'_{H_2O,\lambda_1} & \epsilon'_{Fat,\lambda_1} \\ \epsilon'_{HbO_2,\lambda_2} & \epsilon'_{HHb,\lambda_2} & \epsilon'_{H_2O,\lambda_2} & \epsilon'_{Fat,\lambda_2} \\ \epsilon'_{HbO_2,\lambda_3} & \epsilon'_{HHb,\lambda_3} & \epsilon'_{H_2O,\lambda_3} & \epsilon'_{Fat,\lambda_3} \\ \epsilon'_{HbO_2,\lambda_4} & \epsilon'_{HHb,\lambda_4} & \epsilon'_{H_2O,\lambda_4} & \epsilon'_{Fat,\lambda_4} \\ \epsilon'_{HbO_2,\lambda_5} & \epsilon'_{HHb,\lambda_5} & \epsilon'_{H_2O,\lambda_5} & \epsilon'_{Fat,\lambda_5} \\ \epsilon'_{HbO_2,\lambda_6} & \epsilon'_{HHb,\lambda_6} & \epsilon'_{H_2O,\lambda_6} & \epsilon'_{Fat,\lambda_6} \end{bmatrix} = [[HbO2], [HHb], [H2O], [Fat]] \quad \text{[Math. 6]}$$

$\epsilon^1_{Hbo2,\lambda i}$ may be the inverse matrix absorption coefficient of oxygenated hemoglobin for the i-th wavelength, $\epsilon^1_{HHb,\lambda i}$ may be the inverse matrix absorption coefficient of deoxygenated hemoglobin for the i-th wavelength, $\epsilon^1_{H2O,\lambda i}$ may be the inverse matrix absorption coefficient of moisture for the i-th wavelength, and $\epsilon'_{Fat,\lambda i}$ may be the inverse matrix absorption coefficient of fat for the i-th wavelength. In addition, $[HbO_2]$ may represent the oxygenated hemoglobin content, [HHb] may represent the deoxygenated hemoglobin content, $[H_2O]$ may represent the moisture content, [Fat] may represent the fat content, and $\mu_{\alpha,\lambda i}$ may represent the absorption coefficient for the i-th wavelength. Here, the oxygenated hemoglobin content and the deoxygenated hemoglobin content may be calculated as absolute values in mol units, and the moisture content and fat content may be calculated as relative values in % units.

Looking at some of Math. 6, the content of oxygenated hemoglobin may be expressed as $$[HbO_2] = \mu_{a,\lambda_1}\epsilon'_{HbO_2,\lambda_1} + \mu_{a,\lambda_2}\epsilon'_{HbO_2,\lambda_2} + \mu_{a,\lambda_3}\epsilon'_{HbO_2,\lambda_3} + \mu_{a,\lambda_4}\epsilon'_{HbO_2,\lambda_4} + \mu_{a,\lambda_5}\epsilon'_{HbO_2,\lambda_5} + \mu_{a,\lambda_6}\epsilon'_{HbO_2,\lambda_6}.$$

In this case, the final absorption coefficient 556 may be one of $\mu_{\alpha,\lambda i}$, $\mu_{\alpha,\lambda 2}$, $\mu_{\alpha,\lambda 3}$, $\mu_{\alpha,\lambda 4}$, $\mu_{\alpha,\lambda 5}$, and $\mu_{\alpha,\lambda 6}$. In this way, the content of oxygenated hemoglobin, the content of deoxygenated hemoglobin, the content of moisture, and the content of fat may be estimated using the inverse matrix of the absorption coefficient matrix based on the wavelength-specific absorption coefficient.

Although an example of estimating physiological information 564 using light emitted from a single light source is illustrated in FIG. 5, the present disclosure is not limited thereto. For example, light may be emitted to the body using light sources having different wavelengths, and photodiodes may detect the intensity of the diffuse light. Specifically, a light source group including a light source emitting light of a first wavelength, a light source emitting light of a second wavelength, a light source emitting light of a third wavelength, a light source emitting light of a fourth wavelength, a light source emitting light of a fifth wavelength, and a light source emitting light of a sixth wavelength may be used. In this case, six final absorption coefficients 556 for a specific area may be estimated based on a plurality of pieces of optical data associated with six wavelengths of light. After that, based on the six final absorption coefficients 556 for a specific area, the content of oxygenated hemoglobin, the content of deoxygenated hemoglobin, the content of moisture, and the content of fat for a specific area may be estimated using the inverse matrix of the absorption coefficient matrix.

In summary, one absorption coefficient for a specific area may be estimated based on three pieces of optical data. When light of six different wavelengths is used, six absorption coefficients for a specific area may be estimated based on three pieces of optical data associated with each wavelength, and four pieces of content information (the content of oxygenated hemoglobin, the content of deoxygenated hemoglobin, the content of moisture, and the content of fat) for a specific area may be estimated based on the six absorption coefficients.

FIG. 5 illustrates an example of estimating physiological information 564 using optical data detected by three photodiodes, but the present disclosure is not limited thereto. For example, more than three (for example, 20) photodiodes may be used. In this case, physiological information 564 estimation for a plurality of areas is possible.

The physiological information estimation process for an example of the medical device 100 disclosed in FIG. 1 may be understood through the method described in FIGS. 4 and 5. The optical data structure flow for an example of the medical device 100 disclosed in FIG. 1 will be described in detail later with reference to FIGS. 10 to 12.

Figure 6:
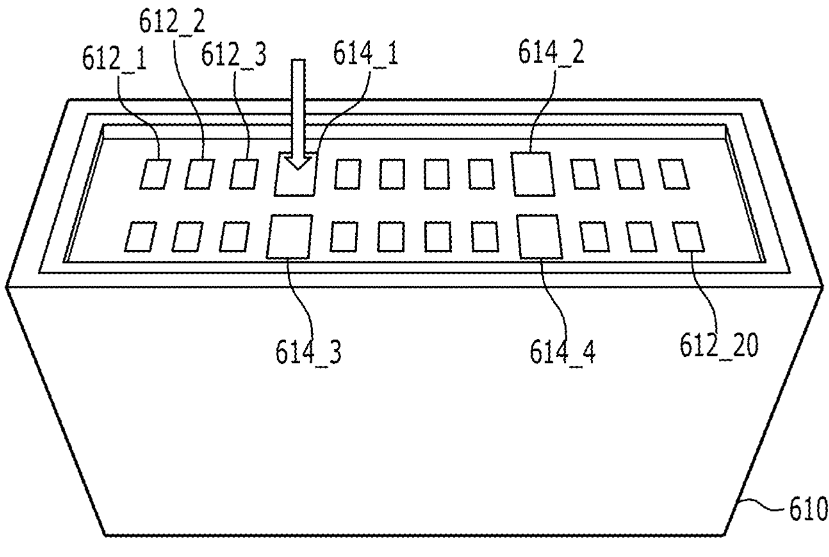
FIG. 6 is a diagram illustrating an example of generating calibration parameters using a calibration box according to an aspect of the present disclosure.

FIG. 6 is a diagram illustrating an example of generating calibration parameters using a calibration box 610 according to an aspect of the present disclosure. In an aspect, a plurality of photodiode openings 612_1 to 612_20 and a plurality of light source group openings 614_1 to 614_4 may be formed on one surface of the calibration box 610. Each of the plurality of photodiode openings 612_1 to 612_20 may correspond to a position of each of the plurality of photodiodes 112_1 to 112_20 included in the medical device 100 disclosed in FIG. 1. In addition, each of the plurality of light source group openings 614_1 to 614_4 may correspond to a position of each of the plurality of light source groups 114_1 to 114_4 included in the medical device 100 illustrated in FIG. 1. In this case, the medical device 100 may be placed in the calibration box 610 so that one surface of the medical device 100 in which a plurality of photodiodes 112_1 to 112_20 and a plurality of light source groups 114_1 to 114_4 are arranged faces one surface of the calibration box 610 in which a plurality of openings 612_1 to 612_20 and 614_1 to 614_4 are formed.

The calibration box 610 is illustrated as having 20 openings for photodiodes 612_1 to 612_20 and four openings for light source groups 614_1 to 614_4, but the present disclosure is not limited thereto. That is, the number of openings formed in the calibration box 610 may be changed depending on the number of photodiodes and the number of light source groups included in the medical device 100 disclosed in FIG. 1.

In an aspect, the calibration box 610 may include a standard reflective object therein. The standard reflective object may diffuse (and/or reflect, hereinafter collectively referred to as "diffuse') the emitted light. In addition, optical information (for example, wavelength-specific diffuse reflectance or the like) regarding the standard reflective object may be defined in advance.

In an aspect, before generating the calibration parameters, a LUT (Look Up Table) may be generated using the calibration box 610. At this time, the LUT may include relative relationship information regarding the intensity of the diffuse light between the plurality of photodiode openings 612_1 to 612_20. Specifically, the LUT may contain information about the ratio of the light intensity of the diffuse light reaching each photodiode opening.

In one example, information included in the LUT may be generated as follows. The first light source may be positioned in the opening 614_1 for the first light source group. Then, a specific photodiode may be positioned in the opening 612_1 for the first photodiode. Here, in order to eliminate the intercept coefficient influence of the system parameter for the specific photodiode, an offset may be set so that the measured voltage value of the specific photodiode becomes 0 when light is not detected by the specific photodiode.

In a state where light is emitted to a standard reflective object by the first light source, a specific photodiode may detect diffuse light. At this time, the measured voltage value of the specific photodiode may be $V_1$. Then, the specific photodiode may be positioned in the opening 612_2 for the second photodiode. In a state where light is emitted to a standard reflective object by the first light source, a specific photodiode may detect diffuse light. At this time, the measured voltage value of the specific photodiode may be $V_2$. Similarly, after positioning a specific photodiode in the third to 20th photodiode openings 612_3 to 612_20, the specific photodiode may measure voltage values of $V_3, V_4, \ldots, V_{20}$ corresponding to the third to 20th photodiode openings 612_3 to 612_20. During the above process, the light intensity of the first light source does not change.

In order to derive the relative relationship of the measured voltage values, one of the voltage values measured in the plurality of photodiode openings 612_1 to 612_20 may be selected as a reference. For example, the voltage value $V_3$ measured at the third photodiode opening 612_3 closest to the first light source group opening 614_1 may be selected as a reference. The ratio of the voltage values measured at each photodiode opening based on the voltage value $V_3$ measured at the third photodiode opening 6123 may be expressed as in Table 2 below.

TABLE 2

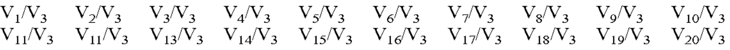

| $V_1/V_3$ | $V_2/V_3$ | $V_3/V_3$ | $V_4/V_3$ | $V_5/V_3$ | $V_6/V_3$ | $V_7/V_3$ | $V_8/V_3$ | $V_9/V_3$ | $V_{10}/V_3$ |
|---|---|---|---|---|---|---|---|---|---|
| $V_{11}/V_3$ | $V_{11}/V_3$ | $V_{13}/V_3$ | $V_{14}/V_3$ | $V_{15}/V_3$ | $V_{16}/V_3$ | $V_{17}/V_3$ | $V_{18}/V_3$ | $V_{19}/V_3$ | $V_{20}/V_3$ |

The ratio of the measured voltage values disclosed in Table 2 may represent the light intensity ratio of the diffuse light. For example, the light intensity of the diffuse light reaching the first photodiode opening 612_1 is equal to the value obtained by multiplying the light intensity of the diffuse light reaching the third photodiode opening 6123 by the ratio of $V_1/V_3$. In this way, when the light intensities of the light sources are the same, the LUT may include information on the light intensity ratio for each position of the diffuse light.

In an aspect, the LUT may store the light intensity ratio information of the diffuse light according to the wavelength of the emitted light in the form of a table. In this case, the LUT may be stored by dividing it into a table associated with a first wavelength (for example, a first light source) and a table associated with a second wavelength (for example, a second light source). For example, when light of six different wavelengths (for example, first to sixth light sources) is used, six tables may be generated for the six wavelengths, and 20 pieces of light intensity ratio information of the diffuse light may be generated for each table.

As may be confirmed in Math. 1 described above, the light intensity of the diffuse light reaching each photodiode may be proportional to the light intensity of the light source. In addition, using the information included in the LUT, the light intensity of the diffuse light reaching another photodiode may be proportional to the light intensity of the diffuse light reaching a specific photodiode. In summary, the light intensity information of the diffuse light reaching each photodiode may be generated by correcting the light intensity information of the light source using the information included in the LUT. An example of the process of correcting the light intensity information of the light source using the information included in the LUT will be described in detail later with reference to FIG. 7.

In an aspect, a calibration parameter may be generated based on the light intensity information of the light source corrected using the LUT. Specifically, the calibration parameter may be generated for each of the plurality of photodiodes. Here, the calibration parameter may include a proportional coefficient and an intercept coefficient.

The calibration parameter generation process will be described based on the plurality of photodiodes 112_1 to 112_20 and the plurality of light source groups 114_1 to 114_4 disclosed in FIG. 1. The medical device 100 may be placed in the calibration box 610 such that one surface of the medical device 100 in which a plurality of photodiodes 112_1 to 112_20 and a plurality of light source groups 114_1 to 114_4 are arranged faces one surface of the calibration box 610 in which a plurality of openings 612_1 to 612_20 and 614_1 to 614_4 are formed.

The first detection process may include a process in which the first photodiode detects diffuse light in a state in which light is emitted to a standard reflective object by the first light source. At this time, the first light source included in the first light source group may emit light first, but the present disclosure is not limited thereto, and one of the second to 24th light sources may emit light first. The first detection process may include a process in which the second photodiode 112_2 detects the diffuse light in a state in which light is emitted to the standard reflective object by the first light source. As a result, the first detection process may include a process in which all of the plurality of photodiodes 112_1 to 112_20 detect the diffuse light in a state in which the light is emitted by the first light source. Here, the light intensity of the first light source may be constant during the first detection process. The second detection process may be the same as the first detection process except that the light intensity of the first light source is changed during the first detection process. Similarly, the third detection process to the n-th detection process in which the light intensity of the first light source is changed may be performed continuously. This detection process may be performed tens of times. In one example, the light intensity of the first light source may be continuously increased or decreased as the detection process progresses.

Through the continuous detection process, a measurement value graph according to the light intensity of the light source may be generated for each photodiode. At this time, a graph of measurement values according to the light intensity of diffuse light may be generated for each photodiode using LUT information. Then, a trend line may be generated for each photodiode based on the graph of measurement values according to the light intensity of diffuse light. Then, a calibration parameter may be generated based on the generated trend line equation. The process of generating a trend line will be described in detail with reference to FIG. 7, and the process of generating calibration parameters based on the trend line equation will be described in detail with reference to FIG. 8.

Figure 7:
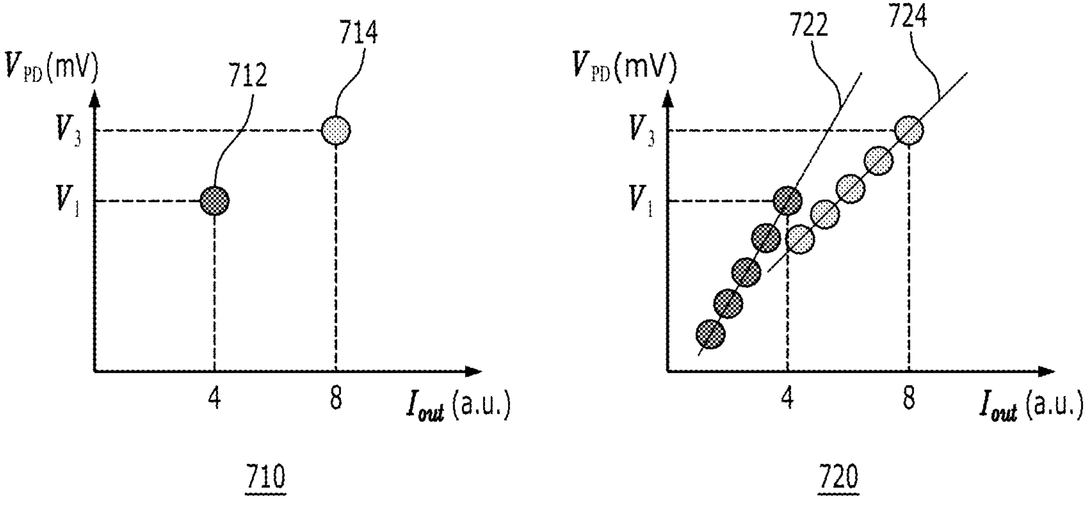
FIG. 7 is a graph illustrating an example of a process for generating calibration parameters according to an aspect of the present disclosure.

FIG. 7 is a graph illustrating an example of a process of generating calibration parameters according to an aspect of the present disclosure. For convenience of explanation, FIG. 7 is described based on two photodiodes illustrated in FIG. 1, that is, the first photodiode 112_1 and the third photodiode 112_3.

The first graph 710 is a graph of measurement values according to the light intensity of diffuse light obtained through the first detection process. The x-axis is the light intensity of the diffuse light, and the y-axis is the measured voltage value. The first measurement value 712 of the first photodiode may be $V_1$, and the first measurement value 714 of the third photodiode may be $V_3$. At this time, $V_1$ and $V_3$ may be different from $V_1$ and $V_3$ of $V_1/V_3$ included in the LUT. Here, the light intensity of the light source at the time of detecting the first measurement value 714 of the third photodiode and the light intensity of the light source at the time of detecting the first measurement value 712 of the first photodiode may be the same.

As described above in FIG. 6, the light intensity of the diffuse light reaching a specific photodiode may be expressed in proportion to the light intensity of the light source. For example, in the first detection process, when the light intensity of the light source is 16 mW, the relative value of the light intensity of the diffuse light reaching the third photodiode 112_3 may be 8 a.u.

In this case, the intensity of the diffuse light reaching the first photodiode 112_1 may be expressed as a relative value based on the intensity of the diffuse light reaching the third photodiode 112_3 based on the information included in the LUT. Specifically, the intensity of the diffuse light reaching the first photodiode 112_1 may be a value obtained by multiplying the intensity of the diffuse light reaching the third photodiode 112_3 by $V_1/V_3$ included in the LUT. In this case, if $V_1/V_3$ included in the LUT is ½, the relative value of the intensity of the diffuse light reaching the third photodiode 112_3 may be 4 a.u. In this way, the intensity information of the diffuse light reaching each photodiode may be generated by correcting the intensity information of the light source using the information included in the LUT.

The second graph 720 is a graph of measurement values according to the intensity of the light of the diffuse light obtained through the first detection process to the fifth detection process. In the illustrated example, the intensity of the light source may decrease as the detection process progresses. Accordingly, the intensity of the light of the diffuse light reaching the third photodiode 112_3 may also decrease in proportion to the intensity of the light source. In addition, the intensity of the light of the diffuse light reaching the first photodiode 112_1 may also decrease in proportion to the intensity of the light of the diffuse light reaching the third photodiode 112_3.

As illustrated in the figure, the trend line 722 of the first photodiode may be generated based on the first to fifth measurement values of the first photodiode. Similarly, the trend line 724 of the third photodiode may be generated based on the first to fifth measurement values of the third photodiode. According to Math. 2, the trend line 722 of the first photodiode may be expressed by an equation such as $V_1=\alpha 1\times I_{out}+\beta 1$. The trend line 724 of the third photodiode may be expressed by an equation such as $V_3=\alpha_3\times I_{out}+\beta 3$.

Similar to the description of the trend lines of the first and third photodiodes described above, trend lines of a plurality of photodiodes may be generated. Then, calibration parameters for the plurality of photodiodes may be generated based on the equations of the generated trend lines. The specific process of generating the calibration parameters will be described in detail later with reference to FIG. 8.

Figure 8:
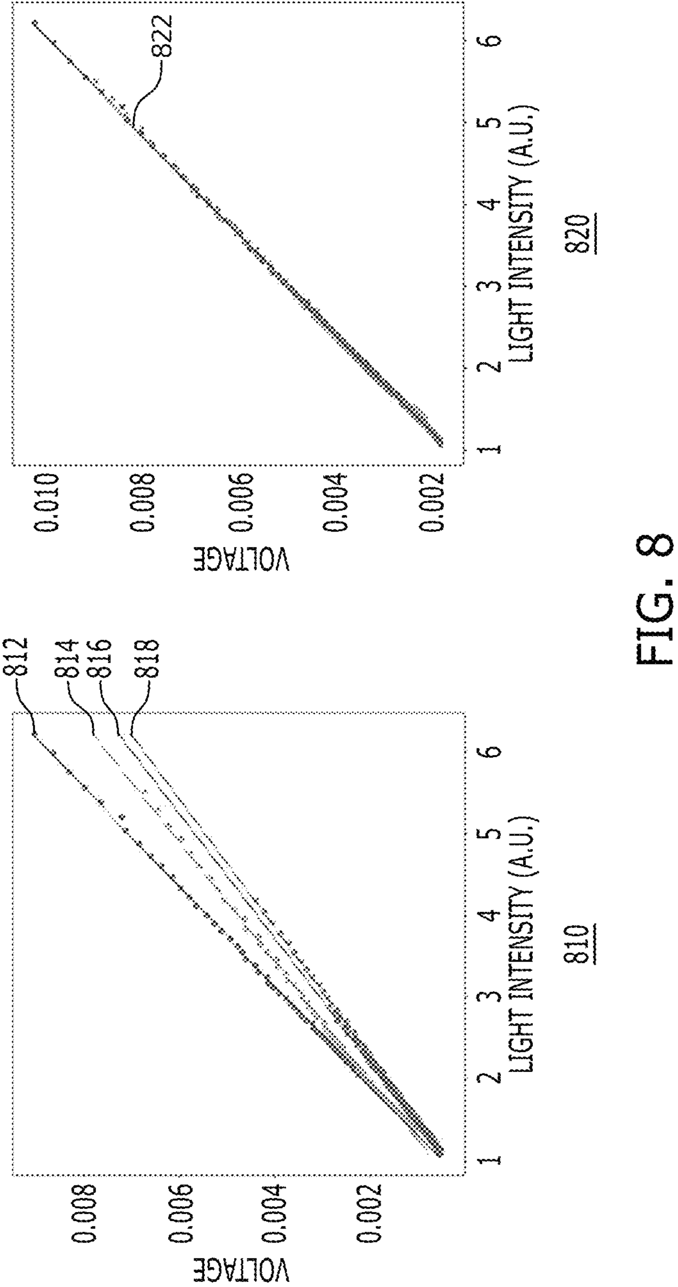
FIG. 8 is a diagram illustrating an example of applying calibration parameters according to an aspect of the present disclosure.

FIG. 8 is a diagram illustrating an example of applying calibration parameters according to an aspect of the present disclosure. The first graph 810 is a graph illustrating trend lines 812, 814, 816, and 818 of a plurality of photodiodes before using the calibration parameter. The x-axis is the light intensity of the diffuse light, and the y-axis is the measured voltage value. Using the first graph 810, the calibration parameter may be generated through Math. 7.

$$V_i' = (V_i - B_i') \times \alpha_i' = (\alpha_i \times I_i + B_i - B_i') \times \alpha_i' = \alpha_n \times I_i \quad \text{[Math. 7]}$$

$V_i'$ may represent a corrected voltage value of the i-th photodiode, $V_i$ may represent a measured voltage value of the i-th photodiode, $\beta_i'$ may represent an intercept coefficient of a calibration parameter for the i-th photodiode, $\alpha_i'$ may represent a proportional coefficient of a calibration parameter for the i-th photodiode, $\alpha_i$ may represent a proportional coefficient of a system parameter for the i-th photodiode, $\beta_i$ may represent an intercept coefficient of a system parameter for the i-th photodiode, and $\alpha_n$ may represent a corrected proportional coefficient.

At this time, the corrected proportional coefficient may be the same for all of the plurality of photodiodes. Specifically, the corrected proportional coefficient may be selected as a value equal to the proportional coefficient of a system parameter of one of the plurality of photodiodes. For example, $\alpha 3$, which is a proportional coefficient of a system parameter according to the equation of the trend line 816 of the third photodiode, may be selected as a corrected proportional coefficient.

The calibration parameter may be generated based on the trend line equation of the photodiode through Math. 7 described above. Specifically, a calibration parameter satisfying $\beta_i'=\beta_i$ and $\alpha_i'=\alpha_n/\alpha_i$ may be generated. For example, the proportional coefficient of the calibration parameter for the first photodiode may satisfy $\alpha_i'=\alpha_n/\alpha 1$. In addition, the intercept coefficient of the calibration parameter for the first photodiode may satisfy $\beta' 1=\beta 1$. The generated calibration parameter may be used to correct a plurality of pieces of optical data as described above in FIG. 4.

In an aspect, the proportional coefficient of the system parameter may be associated with the wavelength of the light source. That is, $\alpha_i$ may be different depending on the wavelength of the light source, and the proportional coefficient of the calibration parameter may be different depending on the proportional coefficient of the system parameter. On the other hand, the intercept coefficient of the system parameter may be independent of the wavelength of the light source, and the intercept coefficient of the calibration parameter may be independent of the wavelength of the light source.

In one example, when using light of six different wavelengths, each photodiode may generate six trend lines associated with light of each wavelength. At this time, the proportional coefficients of the calibration parameters of the six trend lines may be generated one for each, resulting in a total of six. In addition, the proportional coefficients and intercept coefficients of the calibration parameters may be generated for each photodiode. That is, when using light of six different wavelengths and 20 photodiodes, 120 proportional coefficients of the calibration parameters and 20 intercept coefficients of the calibration parameters may be generated.

As described above, calibration parameters for each photodiode may be generated based on the plurality of photodiode trend lines 812, 814, 816, and 818. The second graph 820 shows the trend line 822 corrected using the calibration parameters. As illustrated in the figure, using the calibration parameters, the trend lines 812, 814, 816, and 818 of the plurality of photodiodes before correction may be displayed as one corrected trend line 822. At this time, the equation of the corrected trend line 822 may be $$V_i' = \alpha_n \times I_i.$$

Here, $\alpha_n$ represents a proportional coefficient of the corrected system parameter.

With this configuration, the system parameters for the plurality of photodiodes included in the medical device may be equally corrected. In addition, as described above in FIG. 5, the normalized diffuse reflectance may be calculated based on the system parameters that are identically corrected, and physiological information may be estimated based on the normalized diffuse reflectance. In this way, the medical device according to one or more aspects of the present disclosure may not require additional calibration after performing one calibration parameter generation. That is, one or more aspects of the present disclosure does not require calibration using a phantom, thereby increasing user convenience.

Figure 9:
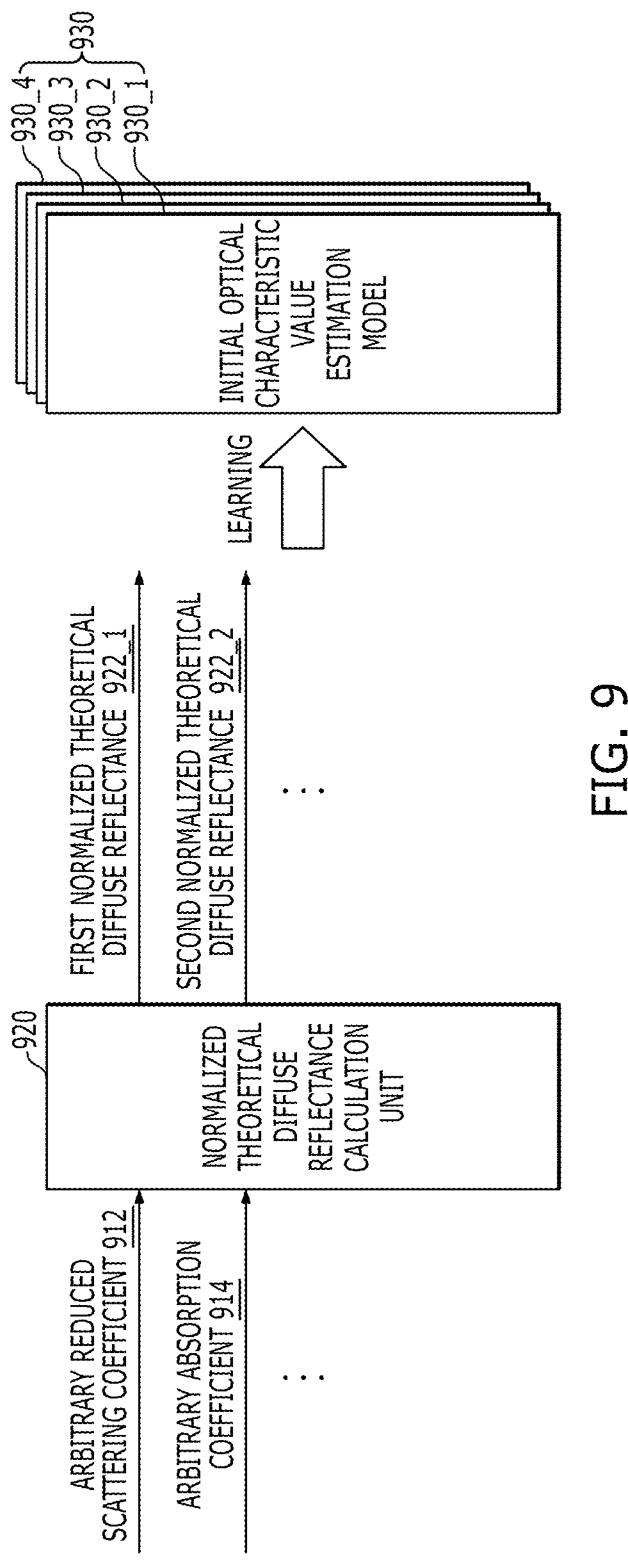
FIG. 9 is a diagram illustrating an example of a learning process of an initial optical characteristic value estimation model according to an aspect of the present disclosure.

FIG. 9 is a diagram illustrating an example of a learning process of an initial optical characteristic value estimation model 930 according to an aspect of the present disclosure. Arbitrary reduced scattering coefficient 912 may be selected as any value within a theoretically possible range as a reduced scattering coefficient. For example, arbitrary reduced scattering coefficient 912 may be selected as any value from 0.5 to 2.00 mm-1. Similarly, arbitrary absorption coefficient 914 may be selected as any value within a theoretically possible range as an absorption coefficient. For example, the arbitrary absorption coefficient 914 may be selected from any value between 0 and 0.08 mm-1.

In an aspect, a normalized theoretical diffuse reflectance calculation unit 920 may calculate the first normalized theoretical diffuse reflectance 922_1 and the second normalized theoretical diffuse reflectance 922_2 based on the arbitrary reduced scattering coefficient 912 and the arbitrary absorption coefficient 914. Specifically, the normalized theoretical diffuse reflectance calculation unit 920 may calculate the normalized theoretical diffuse reflectance from the arbitrary reduced scattering coefficient and the arbitrary absorption coefficient using a diffuse reflectance theoretical equation. The diffuse reflectance theoretical equation may be expressed as Math. 5 described above.

The normalized theoretical diffuse reflectance calculation unit 920 may calculate a pair of normalized theoretical diffuse reflectances based on a pair of optical characteristic values. For example, the pair of optical characteristic values may include an arbitrary reduced scattering coefficient 912 and an arbitrary absorption coefficient 914. In addition, the pair of normalized theoretical diffuse reflectances may include a first normalized theoretical diffuse reflectance 922_1 and a second normalized theoretical diffuse reflectance 922_2. In this case, one piece of learning data may include a pair of optical characteristic values and a pair of normalized theoretical diffuse reflectances.

In an aspect, the normalized theoretical diffuse reflectance calculation process may be as follows. As described above in FIG. 5, the diffuse reflectance theoretical equation may be an equation regarding a reduced scattering coefficient, an absorption coefficient, and a distance between a light source and a photodiode. That is, the first theoretical diffuse reflectance may be calculated based on an arbitrary reduced scattering coefficient 912, an arbitrary absorption coefficient 914, and a first distance between the light source and the first photodiode. Similarly, the second theoretical diffuse reflectance may be calculated based on an arbitrary reduced scattering coefficient 912, an arbitrary absorption coefficient 914, and a second distance between the light source and the second photodiode. In addition, the third theoretical diffuse reflectance may be calculated based on an arbitrary reduced scattering coefficient 912, an arbitrary absorption coefficient 914, and a third distance between the light source and the third photodiode. Here, the first normalized theoretical diffuse reflectance 922_1 may be a value obtained by dividing the second theoretical diffuse reflectance by the first theoretical diffuse reflectance. In addition, the second normalized theoretical diffuse reflectance 922_2 may be a value obtained by dividing the third theoretical diffuse reflectance by the first theoretical diffuse reflectance. At this time, information about the first distance, the second distance, and the third distance may be input in advance into the normalized theoretical diffuse reflectance calculation unit 920.

A plurality of arbitrary reduced scattering coefficients 912 and a plurality of arbitrary absorption coefficients 914 may be generated. A plurality of pairs of normalized theoretical diffuse reflectances may be generated based on each of the plurality of pairs of optical characteristic coefficients. A first set of learning data may be generated based on the plurality of optical characteristic coefficients and the plurality of pairs of normalized theoretical diffuse reflectances corresponding to the optical characteristic coefficient pairs. In one example, the first set of learning data may include 20,000,000 optical characteristic coefficient pairs and normalized theoretical diffuse reflectance pairs.

In an aspect, the first initial optical characteristic value estimation model 9301 may be a deep learning-based model or a machine learning-based model learned using the first set of learning data. Here, the machine learning-based model may be one of KNN (K-Nearest Neighbors), GB (Gradient Boost), and ANN (Artificial Neural Network). The first initial optical characteristic value estimation model 930_1 learned based on the first set of learning data may estimate the initial optical characteristic value (reduced scattering coefficient and absorption coefficient) based on the normalized diffuse reflectance of the second photodiode and the normalized diffuse reflectance of the third photodiode.

In an aspect, the fourth to sixth distances may be distances between the light source and the fourth to sixth photodiodes, respectively. Information about the fourth distance, the fifth distance, and the sixth distance may be input in advance to the normalized theoretical diffuse reflectance calculation unit 920. At this time, the fourth distance, the fifth distance, and the sixth distance may be different from the first distance, the second distance, and the third distance, respectively. In this case, the fourth theoretical diffuse reflectance may be calculated based on an arbitrary reduced scattering coefficient 912, an arbitrary absorption coefficient 914, and a fourth distance between the fourth photodiode and the light source. In addition, the fifth theoretical diffuse reflectance may be calculated based on an arbitrary reduced scattering coefficient 912, an arbitrary absorption coefficient 914, and a fifth distance between the fifth photodiode and the light source. In addition, the sixth theoretical diffuse reflectance may be calculated based on an arbitrary reduced scattering coefficient 912, an arbitrary absorption coefficient 914, and a sixth distance between the sixth photodiode and the light source. Here, the third normalized theoretical diffuse reflectance may be a value obtained by dividing the fifth theoretical diffuse reflectance by the fourth theoretical diffuse reflectance. In addition, the fourth normalized theoretical diffuse reflectance 922_2 may be a value obtained by dividing the sixth theoretical diffuse reflectance by the fourth theoretical diffuse reflectance. A plurality of pieces of learning data generated by repeating this process may be a second set of learning data. The second initial optical characteristic value estimation model 930_2 may be learned based on the second set of learning data.

For the seventh to ninth distances, by repeating the above process, a third set of learning data may be generated. In this case, the third initial optical characteristic value estimation model 9303 may be learned based on the third set of learning data. For the 10th to 12th distances, by repeating the above process, a fourth set of learning data may be generated. In this case, the fourth initial optical characteristic value estimation model 930_4 may be learned based on the fourth set of learning data. Although FIG. 9 illustrates that four initial optical characteristic value estimation models 930_1 to 930_4 are generated, the present disclosure is not limited thereto, and any number of initial optical characteristic value estimation models may be generated depending on the number of photodiodes and the arrangement of the photodiodes and the light source.

When estimating the initial optical characteristic values based on the normalized diffuse reflectance associated with the first distance, the second distance, and the third distance, the first initial optical characteristic value estimation model 930_1 may be used. Similarly, when estimating the initial optical characteristic values based on the normalized diffuse reflectance associated with the fourth distance, the fifth distance, and the sixth distance, the second initial optical characteristic value estimation model 930_2 may be used. When estimating the initial optical characteristic values based on the normalized diffuse reflectance associated with the seventh distance, the eighth distance, and the ninth distance, the third initial optical characteristic value estimation model 930_3 may be used. Similarly, when estimating the initial optical characteristic values based on the normalized diffuse reflectance associated with the 10th distance, the 11th distance, and the 12th distance, the fourth initial optical characteristic value estimation model 930_4 may be used.

If the above-described numerical solver estimates the final reduced scattering coefficient and final absorption coefficient by receiving an arbitrary reduced scattering coefficient 912 and an arbitrary absorption coefficient 914 as initial values, it has the disadvantages of taking too much calculation time and low accuracy. If the initial optical characteristic value estimation model 930 according to one or more aspects of the present disclosure is used to estimate the initial reduced scattering coefficient and the initial absorption coefficient, and then the final reduced scattering coefficient and the final absorption coefficient are estimated using the numerical solver, the calculation time is reduced and the accuracy may be increased. In this way, one or more aspects of the present disclosure has the advantage of providing fast calculation and high accuracy, thereby increasing user convenience.

Figure 10:
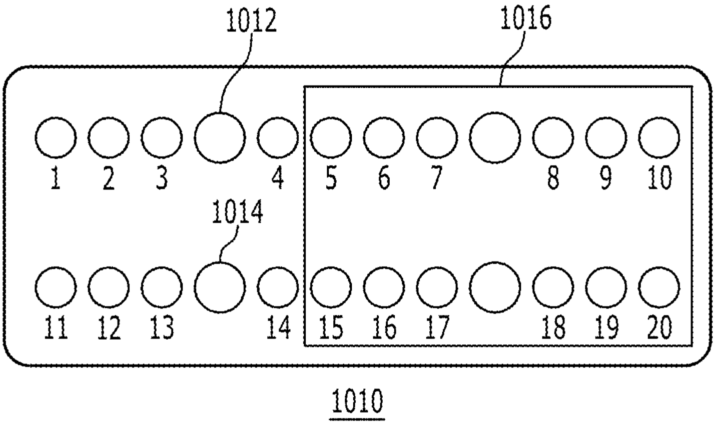
FIG. 10 is a diagram illustrating an example of a medical device according to an aspect of the present disclosure.
Figure 10:
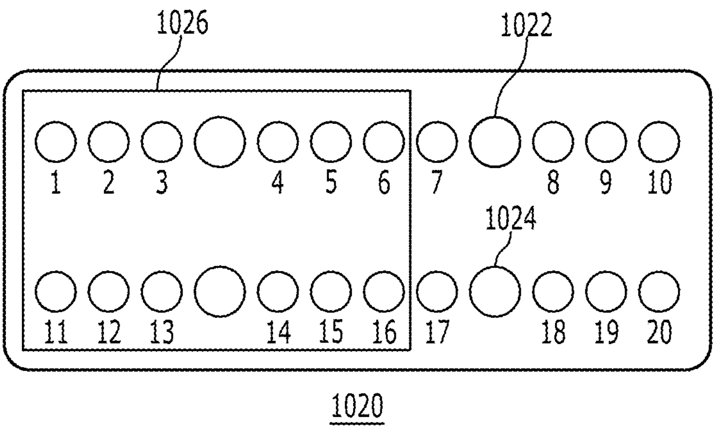

FIG. 10 is a diagram illustrating an example of a medical device according to an aspect of the present disclosure. As illustrated in the figure, a plurality of photodiodes and a plurality of light source groups 1012, 1014, 1022, and 1024 may be arranged on one surface of the medical device. The illustrated example may be the same medical device as the medical device disclosed in FIG. 1. The first light source group 1012 may include six light sources. The six light sources may emit light of different wavelengths. The second to fourth light source groups 1014, 1022, and 1024 may also include six light sources configured to emit light of different wavelengths.

In an aspect, the medical device may be a device that has been calibrated. For example, calibration of the medical device may be performed during the manufacturing process. In addition, the medical device may be attached to the body and used. The process of detecting optical data by a medical device attached to the body will be described in detail.

In an aspect, the first state 1010 may represent a detection relationship between the first light source group 1012 and the third light source group 1014 and the first set of photodiodes 1016. In the first measurement process, each of the first set of photodiodes 1016 may detect diffuse light in a state in which the first light source included in the first light source group 1012 emits light. At this time, the intensity of the first light source may be constant during the first measurement process. After the first measurement process is performed, optical data (twelve measurement voltage values) associated with the first light source may be detected by the first set of photodiodes 1016. Each of the second to sixth measurement processes may be identical to the first measurement process except that the second to sixth light sources included in the first light source group 1012 are used instead of the first light source in the first measurement process. Similarly, the 13th to 18th measurement processes associated with the 13th to 18th light sources included in the third light source group 1014 may be performed.

In an aspect, the second state 1020 may represent a detection relationship between the second light source group 1022 and the fourth light source group 1024 and the second set of photodiodes 1026. In the seventh measurement process, each of the second set of photodiodes 1026 may detect diffuse light in a state in which the seventh light source included in the second light source group 1022 emits light. At this time, the light intensity of the seventh light source may be constant during the seventh measurement process. After the seventh measurement process is performed, optical data (twelve measurement voltage values) associated with the seventh light source may be detected by the second set of photodiodes 1026. Each of the eighth to 12th measurement processes may be identical to the seventh measurement process except that the eighth to 12th light sources included in the second light source group 1022 are used instead of the seventh light source in the seventh measurement process. Similarly, the 19th to 24th measurement processes associated with the 19th to 24th light sources included in the fourth light source group 1024 may be performed.

The process of estimating physiological information based on the optical data obtained through the first to 24th measurement processes will be described in detail later with reference to FIGS. 11 and 12. The physiological information estimated based on the optical data may include oxygenated hemoglobin content information, deoxygenated hemoglobin content information, moisture content information, fat content information, bladder urine volume, and the like.

Figure 11:
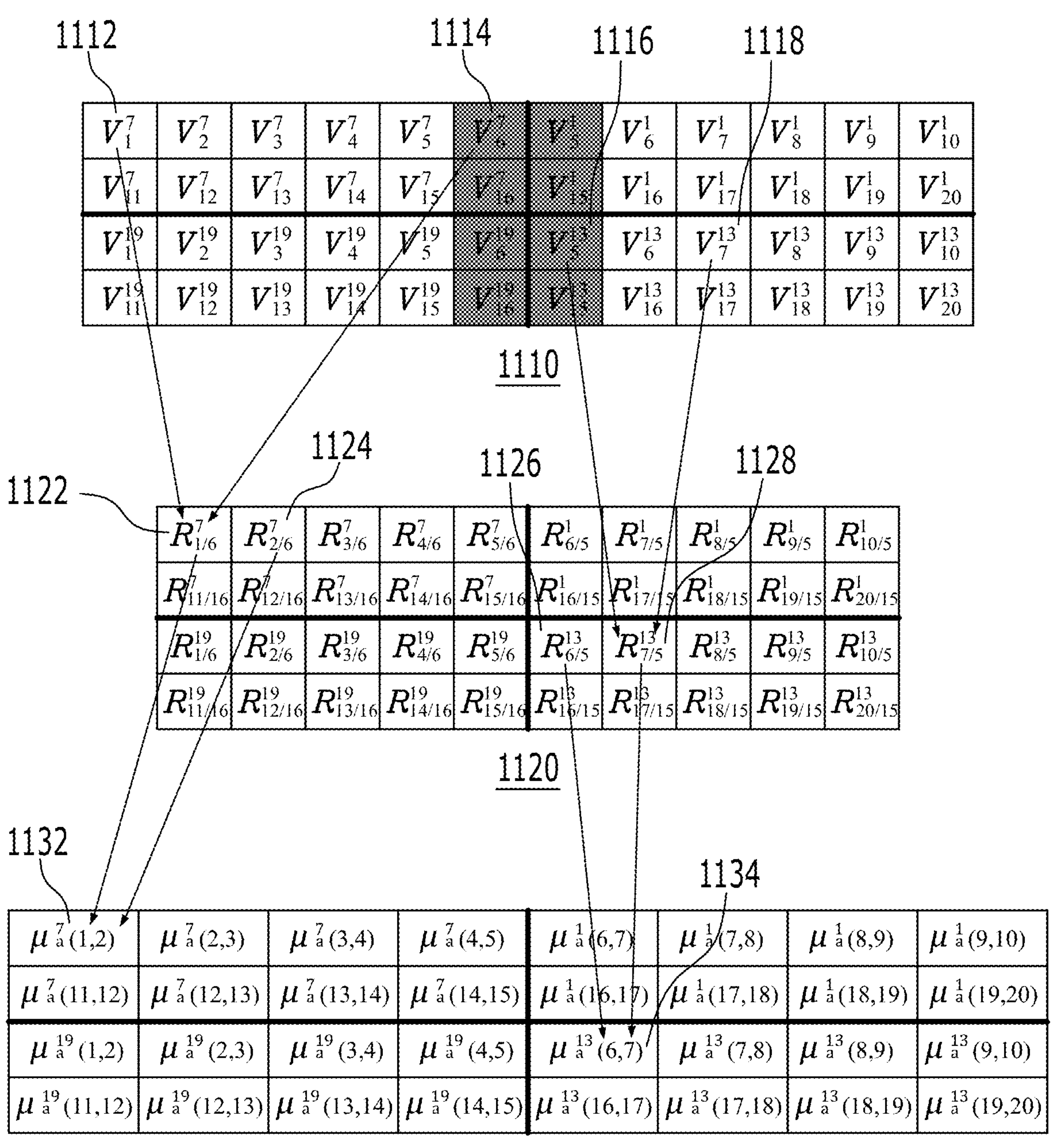
FIG. 11 is a diagram illustrating an example of estimating physiological information based on a plurality of pieces of optical data according to an aspect of the present disclosure.

FIG. 11 is a diagram illustrating an example of estimating physiological information based on a plurality of pieces of optical data according to an aspect of the present disclosure. In FIG. 11, the optical data (measured voltage values) detected through the first measurement process, the seventh measurement process, the 13th measurement process, and the 19th measurement process associated with the first wavelength (that is, the first light source, the seventh light source, the 13th light source, and the 19th light source) among the first to 24th measurement processes described above will be described. The measured voltage values referred to here may represent voltages value corrected using calibration parameters. The optical data associated with the second to sixth wavelengths may be processed in the same manner as the optical data associated with the first wavelength.

In an aspect, a measured voltage data map 1110 may be a data map including the optical data detected through the first measurement process, the seventh measurement process, the 13th measurement process, and the 19th measurement process. Here, the voltage value measured by the x-th photodiode for the y-th light source may be expressed as $V_x^y$. For example, the voltage value 1112 measured by the first photodiode for the seventh light source may be expressed as $V_1^7$.

As described above in FIG. 4, the normalized diffuse reflectance may be calculated by dividing the voltage value of each photodiode by the reference photodiode voltage value. As illustrated in the figure, in the optical data associated with the first light source and the 13th light source, the fifth photodiode and the 15th photodiode closest to the first light source and the 13th light source may be selected as the reference photodiode. For example, in the first row of the plurality of photodiodes associated with the first light source, the fifth photodiode may be selected as the reference photodiode, and in the second row, the 15th photodiode may be selected as the reference photodiode. As illustrated in the figure, the sixth photodiode and the 16th photodiode closest to the seventh and 19th light sources in the optical data associated with the seventh and 19th light sources may be selected as reference photodiodes. For example, in the first row of the plurality of photodiodes associated with the seventh light source, the sixth photodiode may be selected as the reference photodiode, and in the second row, the 16th photodiode may be selected as the reference photodiode.

In an aspect, the normalized diffuse reflectance data map 1120 may be generated based on the measured voltage data map 1110. Here, the normalized diffuse reflectance of the x-th photodiode for the y-th light source may be expressed as $R^{y}_{x/i}$. In this case, i may represent the reference photodiode. In addition, $$R^{y}_{x/i} = V^{y}_{x}/V^{y}_{i}$$

may be satisfied.

As illustrated in the figure, the normalized diffuse reflectance 1122 of the first photodiode for the seventh light source may be generated based on the measured voltage value 1112 of the first photodiode for the seventh light source and the measured voltage value 1114 of the sixth photodiode for the seventh light source. Here, the sixth photodiode may be a reference photodiode. In addition, the normalized diffuse reflectance 1128 of the seventh photodiode for the 13th light source may be generated based on the measured voltage value 1116 of the fifth photodiode for the 13th light source and the measured voltage value 1118 of the seventh photodiode for the 13th light source. Here, the fifth photodiode may be a reference photodiode.

In an aspect, the normalized diffuse reflectance data map 1120 may have a smaller number of pieces of data than the measured voltage data map 1110. Specifically, the normalized diffuse reflectance for a specific reference photodiode may not be calculated. For example, the normalized diffuse reflectance for the measured voltage value 1116 of the fifth photodiode for the 13th light source may not be calculated. Here, the fifth photodiode may be a reference photodiode. In the illustrated example, if the number of pieces of data of the measured voltage data map 1110 is 48 (4×12) and the number of measured voltage values corresponding to the reference photodiode is 8, the number of pieces of data of the normalized diffuse reflectance may be 40.

The reduced scattering coefficient may be associated with a specific area. Here, the reduced scattering coefficient may be a final reduced scattering coefficient. In one example, the first area may be a body part associated with the first photodiode and the second photodiode. Similarly, the n-th area may be a body part associated with the n-th photodiode and the (n+1)th photodiode.

In an aspect, the reduced scattering coefficient data map 1130 may be derived based on the normalized diffuse reflectance data map 1120. The reduced scattering coefficient may be estimated based on two normalized diffuse reflectances using the method described in FIG. 5. The reduced scattering coefficient of the n-th area for the y-th light source may be expressed as $$\mu^{y}_{\alpha}(n, n+1).$$

In one example, the reduced scattering coefficient of the n-th area for the y-th light source may be estimated based on the normalized diffuse reflectance of the n-th photodiode for the y-th light source and the normalized diffuse reflectance of the (n+1)th photodiode for the y-th light source. For example, the reduced scattering coefficient 1132 of the first area for the seventh light source may be estimated based on the normalized diffuse reflectance 1122 of the first photodiode for the seventh light source and the normalized diffuse reflectance 1124 of the second photodiode for the seventh light source. In another example, the reduced scattering coefficient 1134 of the sixth area for the 13th light source may be estimated based on the normalized diffuse reflectance 1126 of the sixth photodiode for the 13th light source and the normalized diffuse reflectance 1128 of the seventh photodiode for the 13th light source.

Similarly, the absorption coefficient data map may be derived based on the normalized diffuse reflectance data map 1120. Here, the absorption coefficient may be a final absorption coefficient. Since the absorption coefficient is apart of physiological information, the absorption coefficient data map may be used as physiological information.

In an aspect, the reduced scattering coefficient data map 1130 may have a smaller number of pieces of data than the normalized diffuse reflectance data map 1120. Specifically, one reduced scattering coefficient may be estimated based on two normalized diffuse reflectances. For example, if the number of normalized diffuse reflectance data maps 1120 is 40 (4×10), the number of reduced scattering coefficient data maps 1130 may be 32 (4×8). The absorption coefficient data map may also have a smaller number of pieces of data than the normalized diffuse reflectance data map 1120.

Based on the above, the reduced scattering coefficient data map and the absorption coefficient data map may be calculated for a plurality of pieces of optical data detected after the first to 24th measurement processes are performed. In an aspect, the reduced scattering coefficient data map and the absorption coefficient data map may be generated for each wavelength. For example, the reduced scattering coefficient data map and the absorption coefficient data map for the second wavelength may be generated for a plurality of pieces of optical data detected after the second measurement process, the eighth measurement process, the 14th measurement process, and the 20th measurement process associated with the second wavelength are performed. Similarly, the reduced scattering coefficient data map and the absorption coefficient data map for the n-th wavelength may be generated for a plurality of pieces of optical data detected after the plurality of measurement processes associated with the n-th wavelength are performed. The process of generating a physiological information data map based on the plurality of reduced scattering coefficient data maps will be described in detail below with reference to FIG. 12.

Figure 12:
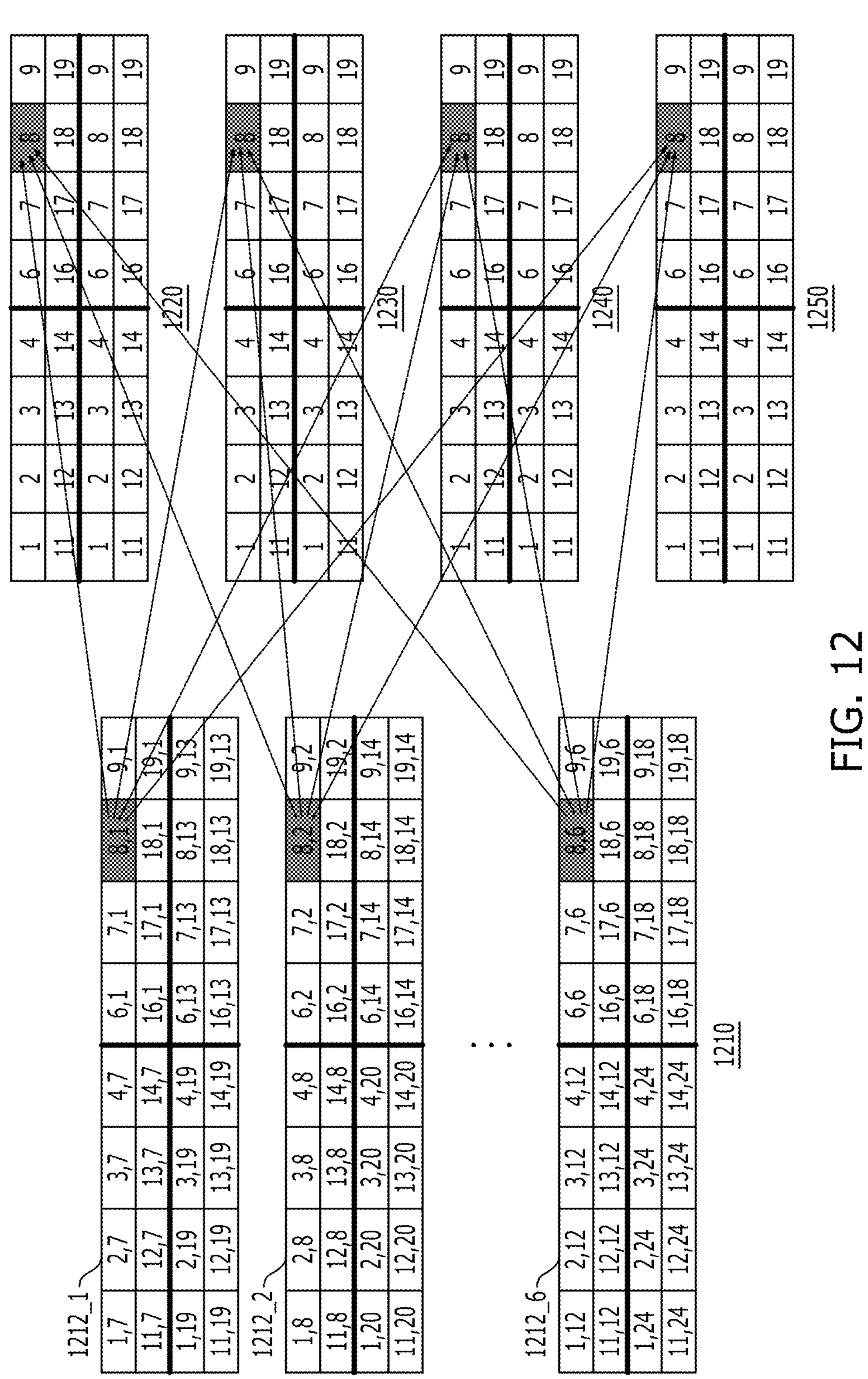
FIG. 12 is a diagram illustrating an example of estimating physiological information based on a plurality of reduced scattering coefficient data maps according to an aspect of the present disclosure.

FIG. 12 is a diagram illustrating an example of estimating physiological information based on a plurality of reduced scattering coefficient data maps according to an aspect of the present disclosure. The plurality of reduced scattering coefficient data maps 1210 may include reduced scattering coefficient data maps for each wavelength. In an aspect, the reduced scattering coefficient data map 1212_1 for the first wavelength may include all reduced scattering coefficients estimated based on a plurality of pieces of optical data detected by performing a plurality of measurement processes associated with the first wavelength. Similarly, the reduced scattering coefficient data maps 1212_2 to 1212_6 for the second to sixth wavelengths may be identical to the reduced scattering coefficient data map 1212_1 for the first wavelength except that the reduced scattering coefficient data map 1212_1 for the first wavelength is based on a plurality of pieces of optical data detected by performing a plurality of measurement processes associated with the second to sixth wavelengths, respectively, instead of the first wavelength. Here, the reduced scattering coefficient may represent the final reduced scattering coefficient. In the illustrated example, the reduced scattering coefficient of the x-th area for the y-th light source may be represented by x,y.

In an aspect, a physiological information data map may be derived based on a plurality of reduced scattering coefficient data maps 1210. Specifically, physiological information may be estimated based on a plurality of reduced scattering coefficients of a specific area for light sources associated with different wavelengths. For a method of estimating physiological information based on the reduced scattering coefficient, reference may be made to the description in FIG. 5.

For example, physiological information for the x-th area may be estimated based on the reduced scattering coefficients of [(x,y), (x,y+1), (x,y+2), (x,y+3), (x,y+4), (x,y+5)]. Here, (x,y) may be the reduced scattering coefficient of the x-th area for the y-th light source, which is included in the reduced scattering coefficient data map 1212_1 for the first wavelength. Specifically, physiological information (for example, oxygenated hemoglobin content information, deoxygenated hemoglobin content information, moisture content information, fat content information, and the like) for the eighth area may be estimated based on the reduced scattering coefficient of the eighth area for the first light source, the reduced scattering coefficient of the eighth area for the second light source, the reduced scattering coefficient of the eighth area for the third light source, the reduced scattering coefficient of the eighth area for the fourth light source, the reduced scattering coefficient of the eighth area for the fifth light source, and the reduced scattering coefficient of the eighth area for the sixth light source. Here, each of the first to sixth light sources may emit light of the first to sixth wavelengths, respectively.

In an aspect, the plurality of physiological information data maps may include a first physiological information data map 1220, a second physiological information data map 1230, a third physiological information data map 1240, and a fourth physiological information data map 1250. Here, each of the first to fourth physiological information data maps 1220, 1230, 1240, and 1250 may be one of an oxygenated hemoglobin ($HbO_2$) data map, a deoxygenated hemoglobin (HHb) data map, a moisture ($H_2O$) data map, and a fat (Fat) data map.

In an aspect, the plurality of physiological information data maps 1220, 1230, 1240, and 1250 may have a smaller number of pieces of data than the plurality of reduced scattering coefficient data maps 1210. Specifically, four pieces of physiological information may be estimated based on six pieces of data included in a plurality of physiological information data maps. For example, each of the plurality of reduced scattering coefficient data maps 1210 includes 32 (4×8) pieces of data, so that the plurality of reduced scattering coefficient data maps 1210 may include 192 (4×8×6) pieces of data. At this time, the plurality of physiological information data maps 1220, 1230, 1240, and 1250 may include 128 (4×8×4) pieces of data.

Physiological information for a plurality of areas may be provided using a plurality of light sources and a plurality of photodiodes. One or more aspects according to the present disclosure may provide physiological information for not only a local area of the body but also a wide area of the body. In addition, by providing physiological information for a plurality of areas, the state of an organ included in the body (for example, the urine volume stored in the bladder, the location of the bladder, and the like) may be specifically identified. For patients who do not feel the urge to urinate, physiological information about their bladder may be provided in real-time or periodically using one or more aspects according to the present disclosure. The patient may monitor the urine volume stored in their bladder through the provided information and urinate at an appropriate time.

Figure 13:
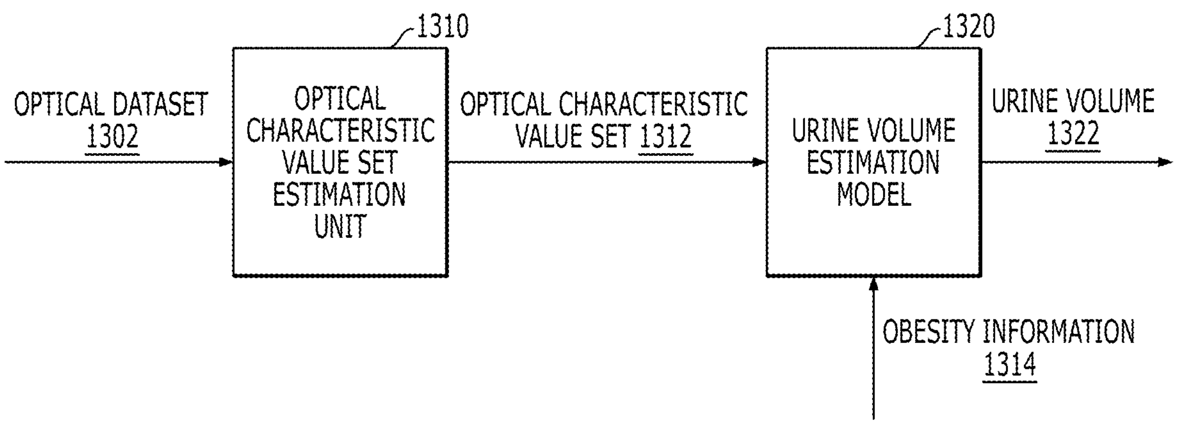
FIG. 13 is a block diagram illustrating an example of a method of estimating a bladder urine volume according to an aspect of the present disclosure.

FIG. 13 is a block diagram illustrating an example of a method of estimating the bladder urine volume according to an aspect of the present disclosure. In the content described below with reference to FIGS. 13 to 16, a “measurement cycle” may refer to a series of processes for detecting an optical dataset using a medical device (for example, the medical device 100 described with reference to FIG. 1) placed on the skin located over the bladder of a specific user. That is, the measurement cycle may include the first to 24th measurement processes described with reference to FIG. 10. The detailed process of the measurement cycle may be understood through the content described with reference to FIGS. 1 and 10.

In an aspect, the processor may receive an optical dataset 1302 associated with a specific user by performing a measurement cycle. For example, the optical dataset 1302 may include the measured voltage data map 1110 described above in FIG. 11. For example, the optical dataset 1302 may include 48 pieces of optical data for each of six wavelengths.

In an aspect, the optical characteristic value set estimation unit 1310 may estimate an optical characteristic value set for at least a part of the body of the specific user based on the optical dataset 1302. Here, the processor may utilize the optical characteristic value set estimation unit 1310. For example, the optical characteristic value set estimation unit 1310 may derive a normalized diffuse reflectance set associated with a plurality of photodiodes based on the optical dataset 1302. In addition, the optical characteristic value set estimation unit 1310 may estimate the optical characteristic value set 1312 associated with at least a part of the body based on the normalized diffuse reflectance set. A series of processes performed by the optical characteristic value set estimation unit 1310 may be understood based on the contents described with reference to FIGS. 4 to 12.

In one example, the optical characteristic value set 1312 may include the final reduced scattering coefficient 554 and the final absorption coefficient 556 described with reference to FIG. 5. For example, the optical characteristic value set 1312 may include the reduced scattering coefficient data map 1130 and the absorption coefficient data map described with reference to FIG. 11. For example, the optical characteristic value set 1312 may include 32 pairs of reduced scattering coefficients and absorption coefficients for each of six wavelengths.

In an aspect, a urine volume estimation model 1320 may estimate the bladder urine volume 1322 of a specific user based on the optical characteristic value set 1312. At this time, the urine volume estimation model 1320 may be a deep learning-based model or a machine learning-based model that has learned a plurality of learning datasets. For example, the machine learning-based model may be an ANN (Artificial Neural Network), KNN (K-Nearest Neighbors), GB (Gradient Boost), a linear regression model, a random forest model, or an Ada Boost model. In addition, the learning dataset may include a pair of an actual urine volume and an optical characteristic value set associated with the actual urine volume. The process of obtaining the learning dataset and the process of the urine volume estimation model 1320 learning a plurality of learning datasets will be described in detail with reference to FIGS. 14 and 15.

In another embodiment, the urine volume estimation model 1320 may estimate the bladder urine volume 1322 of the user based on the optical characteristic value set 1312 and the obesity information 1314. Here, the urine volume estimation model 1320 may be a deep learning-based model or a machine learning-based model that has learned a plurality of learning datasets and learning obesity information. In this case, the obesity information may include information about fat in the body surrounding the bladder. For example, the obesity information may include a body mass index (BMI), obesity measured by an abdominal obesity measurement method, obesity measured by a standard weight method, a body fat index, abdominal fat thickness measured using ultrasound, and the like. In another example, the obesity information may include the absorption coefficient described above. With this configuration, the urine volume estimation model 1320 learns the obesity information 1314, so that the urine volume estimation model 1320 may accurately estimate the urine volume even in the case of an obese user.

In an aspect, the processor may calculate a physiological information set based on the optical characteristic value set 1312. The process of calculating the physiological information set may be understood based on the content described with reference to FIG. 12. Here, the physiological information set may correspond to the optical characteristic value set 1312. For example, the physiological information set may include absorption coefficient data included in the absorption coefficient data map. In addition, the physiological information set may include a plurality of physiological information data maps 1220, 1230, 1240, and 1250 calculated based on the plurality of reduced scattering coefficient data maps 1210 described with reference to FIG. 12. In this case, the processor may estimate the urine volume 1322 using the physiological information set corresponding to the optical characteristic value set 1312 together with the optical characteristic value set 1312. However, since the physiological information set can be calculated based on the optical characteristic value set 1312, it is described based on the optical characteristic value set 1312.

For users with significant fat around the skin where the bladder is located, the optical data included in the optical dataset 1302 may show little changes even if the bladder urine volume increases or decreases. In an aspect, if the amount of change in the optical data included in the optical dataset 1302 is extremely small even if the bladder urine volume increases or decreases, the processor may output a result associated with the inability to estimate the urine volume. For example, if the obesity information 1314 is higher than a predetermined obesity reference value, the processor may output a result associated with the inability to estimate the urine volume.

In an aspect, if the estimated urine volume 1322 is greater than a predetermined threshold, the processor may output a message recommending voiding. For example, the threshold may correspond to the bladder urine volume at which a person feels the urge to urinate on average. Specifically, the processor may output visual, auditory, and tactile information as a message recommending voiding through the user terminal or the medical device. For example, the user terminal or the medical device may output a pop-up window or a vibration and/or sound notification recommending voiding. With this configuration, patients wearing the medical device may be provided with a message recommending voiding, thereby allowing them to void at an appropriate time.

The measurement cycle may be performed in real-time or periodically. One or more aspects according to the present disclosure may provide the patient with the estimated urine volume 1322 based on the optical dataset 1302 detected through the measurement cycle. The patient may be provided with the bladder urine volume in real-time or periodically. That is, the patient may monitor the urine volume stored in their bladder through the provided information and urinate at an appropriate time.

Figure 14:
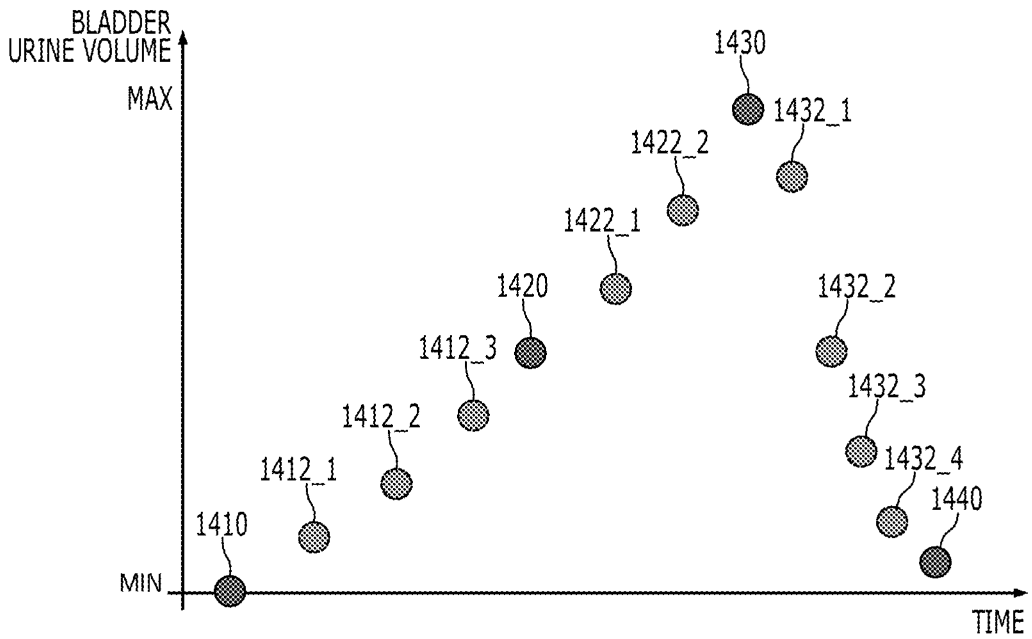
FIG. 14 is a graph illustrating an example of learning data according to an aspect of the present disclosure.

FIG. 14 is a graph illustrating an example of learning data according to an aspect of the present disclosure. In an aspect, the processor may receive an optical dataset associated with the n-th measurement through the n-th measurement cycle (where n is 1, 2, 3, 4 or more). The processor may estimate the optical characteristic value of the n-th measurement based on the optical dataset of the n-th measurement. In this case, the n-th actual urine volume may be a value that directly measures the bladder urine volume of a specific user at the time when the n-th measurement cycle was performed. For example, the actual urine volume may be obtained through a bladder irrigation process, a urodynamic study (UDS) process, a clean intermittent Catheterization (CIC) process, and the like.

In one example, the actual urine volume may be obtained through a bladder irrigation process. Specifically, the bladder irrigation process may include draining urine in the bladder of a specific user using a polycatheter. At this time, the bladder urine volume of the specific user may be specifically confirmed through an ultrasonic bladder urine volume device (RU scanner, Residual Urine Scanner). Thereafter, the bladder irrigation process may inject sterile saline into the bladder of the specific user. At this time, the actual urine volume may correspond to the volume of the injected sterile saline. For example, if the entire urine in the bladder of the specific user is drained, the first actual urine volume may be approximately 0 ml. Thereafter, if 100 ml of sterile saline is injected into the bladder of the specific user, the second actual urine volume may be 100 ml.

In another example, the actual urine volume may be obtained through a urodynamic study process. Specifically, the urodynamic study process may include a bladder irrigation process using a polycatheter for UDS instead of a polycatheter. The actual urine volume may be obtained through the bladder irrigation process included in the urodynamic study process. In addition, various pieces of measurement data such as the internal pressure of the bladder, the activity of the bladder muscle, and the connection status of the urethra and the bladder may be obtained through the urodynamic study process. In one example, the learning dataset may include the corresponding measurement data.

In another example, the actual urine volume may be obtained through the clean intermittent Catheterization process. Specifically, the clean intermittent Catheterization process may include draining urine in the bladder using a clean intermittent catheter. At this time, the urine volume drained using the clean intermittent catheter may be measured (for example, measuring the urine volume drained through a Catheterization cup). At this time, the actual urine volume may be calculated through the urine volume drained. For example, the entire bladder urine volume may be drained twice through the clean intermittent Catheterization process. In the first time, 200 ml of urine in the bladder may be drained, and in the second time, 150 ml of urine in the bladder may be drained. In this case, the first actual urine volume may be 350 ml, the second actual urine volume may be 150 ml, and the third actual urine volume may be 0 ml.

In one example, a plurality of actual urine volumes may be obtained. For example, a first actual urine volume corresponding to the minimum bladder urine capacity of a specific user may be obtained. In addition, an X-th actual urine volume corresponding to the minimum bladder urine capacity of a specific user may be obtained (where x is 2, 3, or more). When x is 3 or more, the second to (X−1)th actual urine volumes may be obtained as values between the first actual urine volume and the X-th actual urine volume.

In the graph of FIG. 14, the x-axis may be time and the y-axis may be the bladder urine volume of a specific user. Referring to FIG. 14, the actual urine volume included in each of the first learning data 1410, the second learning data 1420, the third learning data 1430, and the fourth learning data 1440 may be displayed. Specifically, the first learning data 1410 may include the first actual urine volume at the time when the first measurement cycle was performed. Similarly, the n-th learning data may include the n-th actual urine volume at the time when the n-th measurement was performed. Additionally, the n-th learning data may include a pair of the n-th actual urine volume and the optical characteristic value of the n-th measurement. FIG. 14 illustrates only the first learning data 1410 to the fourth learning data 1440, but the present disclosure is not limited thereto. For example, a plurality of pieces of learning data may be obtained through either more than four or fewer than four measurement cycles.

The minimum bladder urine capacity of a specific user may correspond to the urine volume at the time when the entire urine in the bladder was drained. For example, the minimum bladder urine capacity of a specific user may be about 0 ml. In addition, the maximum bladder urine capacity of a specific user may correspond to the maximum capacity of the bladder. For example, the maximum bladder urine capacity of a specific user may be about 400 ml to 500 ml. The minimum urine capacity and the maximum bladder urine capacity of a specific user may vary from user to user. Referring to FIG. 14, the first actual urine volume may correspond to the minimum bladder urine capacity of a specific user, and the third actual urine volume may correspond to the maximum bladder urine capacity of a specific user.

In an aspect, a teacher model may be generated by learning a plurality of learning datasets. For example, the teacher model may use a linear regression model, a random forest model, and the like. In addition, the teacher model may estimate an additional learning optical characteristic value set by receiving an additional learning urine volume.

In one example, the n-th teacher model may be a teacher model that has learned the (n+1)th learning dataset and the n-th learning dataset. Here, the additional learning urine volume of the n-th estimation may be a random value selected between the (n+1)th actual urine volume and the n-th actual urine volume. Here, the n-th estimation may represent a process of estimating an additional learning optical characteristic value set of a plurality of n-th estimations using the n-th teacher model based on the additional learning urine volumes of the plurality of n-th estimations between the (n+1)th actual urine volume and the n-th actual urine volume. For example, the plurality of additional learning urine volumes of the n-th estimation may be values selected at a certain interval between the (n+1)th actual urine volume and the n-th actual urine volume. For example, if the (n+1)th actual urine volume is 400 ml and the n-th actual urine volume is 100 ml, the first additional learning urine volume of the n-th estimation may be selected as 200 ml, and the second additional learning urine volume of the n-th estimation may be selected as 300 ml.

For example, the first estimation may include a process of estimating a first additional learning optical characteristic value set based on a first additional learning urine volume between the second actual urine volume and the first actual urine volume. Similarly, the first estimation may include a process of estimating a kth additional learning optical characteristic value set based on a kth additional learning urine volume between the second actual urine volume and the first actual urine volume (where k is 1, 2, 3, or more). In this case, the first additional learning dataset of the first estimation may include the first additional learning urine volume and the first additional learning optical characteristic value set. Similarly, the kth additional learning dataset of the first estimation may include the kth additional learning urine volume and the kth additional learning optical characteristic value set.

Referring to the graph of FIG. 14, the additional learning urine volumes included in each of the first additional learning dataset 1412_1 of the first estimation, the second additional learning dataset 1412_2 of the first estimation, and the third additional learning dataset 1412_3 of the first estimation may be displayed. Specifically, the first additional learning urine volume of the first estimation to the third additional learning urine volume of the first estimation may be displayed between the first actual urine volume and the second actual urine volume. In one example, each time point for the first additional learning dataset 1412_1 of the first estimation to the third additional learning dataset 1412_3 of the first estimation may correspond to a method in which the additional learning urine volume is selected between the second actual urine volume and the first actual urine volume. For example, if the plurality of additional learning urine volumes are selected as values at a constant interval between the second actual urine volume and the first actual urine volume, each time point for the first additional learning dataset 1412_1 of the first estimation to the third additional learning dataset 1412_3 of the first estimation may be selected as a value at a constant interval between the second actual urine volume measurement time point and the first actual urine volume measurement time point. For example, if the second actual urine volume is 400 ml, the time point corresponding to the first learning data 1410 is 0 seconds, the first actual urine volume is 0 ml, the time point corresponding to the second learning data 1420 is 4000 seconds, the first additional learning urine volume of the first estimation is 100 ml, the second additional learning urine volume of the first estimation is 200 ml, and the third additional learning urine volume of the first estimation is 300 ml, then the time point corresponding to the first additional learning dataset 1412_1 of the first estimation may be 1,000 seconds, the time point corresponding to the second additional learning dataset 1412_2 of the second estimation may be 2,000 seconds, and the time point corresponding to the third additional learning dataset 1412_3 of the first estimation may be 3,000 seconds.

Based on the above description of the first estimation between the second learning data 1420 and the first learning data 1410, the second estimation between the third learning data 1430 and the second learning data 1420, and the third estimation between the fourth learning data 1440 and the third learning data 1430 may also be understood in the same way.

Although FIG. 14 illustrates three additional learning datasets 1412_1 to 1412_3 of the first estimation, one or more aspects of the present invention is not limited thereto.

For example, if the number of additional learning urine volumes is selected to be more than or less than three, more than or less than three additional learning datasets may also be generated. In addition, although FIG. 14 illustrates that four measurement cycles are performed, one or more aspects of the present invention is not limited thereto. For example, measurements may be performed more than or less than four times. In another example, a plurality of measurements may be performed over 72 hours.

In an aspect, if two measurement cycles are performed, two learning datasets may be obtained. For example, the first urine volume included in the first learning dataset may correspond to the minimum urine volume of the bladder of a specific user, and the second urine volume included in the second learning dataset may correspond to the maximum urine volume of the bladder of a specific user. In this case, a personalized urine volume prediction model may be generated by minimizing data collection for the user to minimize user inconvenience.

In another embodiment, when the measurement cycle is performed a plurality of times (for example, three or more times), a plurality of learning datasets may be obtained. In this case, a plurality of teacher models may be generated based on the plurality of learning datasets, and a plurality of additional learning datasets may be generated based on the plurality of teacher models. The urine volume prediction model may increase the accuracy of estimating the bladder urine volume by learning the plurality of learning datasets and the plurality of additional learning datasets.

Figure 15:
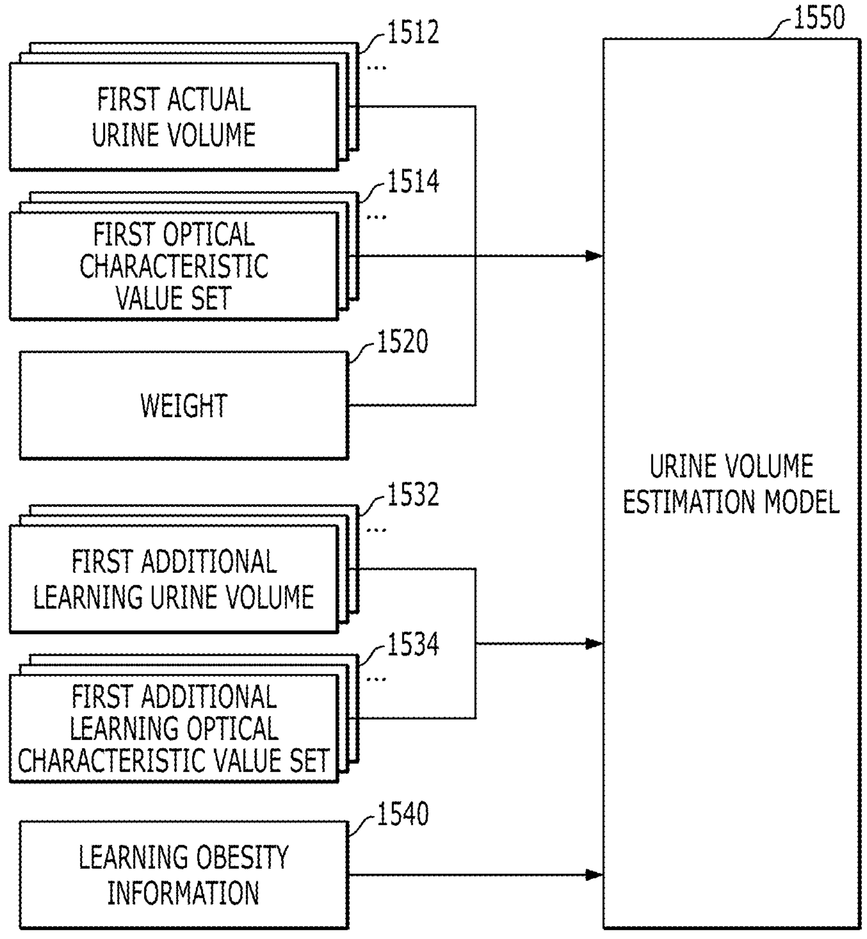
FIG. 15 is a block diagram illustrating an example of a urine volume estimation model according to an aspect of the present disclosure.

FIG. 15 is a block diagram illustrating an example of a urine volume estimation model 1550 according to an aspect of the present disclosure. In an aspect, the urine volume estimation model 1550 may learn a plurality of learning datasets 1512 and 1514. Here, the n-th learning dataset may include a pair of the n-th actual urine volume and the n-th optical characteristic value set. That is, the plurality of learning datasets 1512 and 1514 may include a plurality of actual urine volumes 1512 and a plurality of optical characteristic value sets 1514. The method of obtaining the plurality of learning datasets may be understood through learning data 1410, 1420, 1430, and 1440 described with reference to FIG. 14.

In an aspect, the urine volume estimation model 1550 may further learn a single or a plurality of additional learning datasets 1532 and 1534. Here, the k-th additional learning data may include a pair of the k-th additional learning urine volume and the k-th additional learning optical characteristic value set. That is, the plurality of additional learning datasets 1532 and 1534 may include a plurality of additional learning urine volumes 1532 and a plurality of additional learning optical characteristic value sets 1534. The method of obtaining a plurality of additional learning datasets may be understood through the plurality of additional learning datasets 1412_1 to 1412_3, 1422_1, 1422_2, and 1432_1 to 1432_4 described with reference to FIG. 14. In FIG. 15, a plurality of pairs of additional learning urine volumes and additional learning optical characteristic value sets are illustrated, but the present disclosure is not limited thereto, and there may be one pair of an additional learning urine volume and an additional learning optical characteristic value set.

In an aspect, the urine volume estimation model 1550 may be learned by applying a weight 1520 to a plurality of learning datasets 1512 and 1514. Specifically, the weight 1520 may be information for the urine volume estimation model 1550 to adjust the learning weight of the plurality of additional learning datasets 1532 and 1534 and the plurality of learning datasets 1512 and 1514. For example, the weight 1520 may be determined in advance before the urine volume estimation model 1550 learns data. Alternatively or additionally, the weight 1520 may be applied to the plurality of additional learning datasets and adjusted during the learning process of the urine volume estimation model 1550.

In an aspect, the urine volume estimation model 1550 may further learn learning obesity information 1540. At this time, the learning obesity information 1540 may be obesity information of a body that is the target of measurement of the plurality of actual urine volumes 1512. FIG. 15 illustrates a single piece of learning obesity information 1540, but the present disclosure is not limited thereto. For example, if a plurality of actual urine volumes 1512 are measured for a plurality of bodies, the urine volume estimation model 1550 may learn a plurality of pieces of learning obesity information.

The urine volume estimation model 1550 may learn by applying the weight 1520 to a plurality of learning datasets 1512 and 1514, thereby focusing on a plurality of actual urine volumes 1512. As a result, the urine volume estimation model 1550 can accurately estimate the urine volume. In addition, the urine volume estimation model 1550 may be provided in a customized manner for each user by learning the learning obesity information 1540. In addition, since the urine volume estimation model 1550 uses a machine learning model or a deep learning model that is relatively well supported for application development, one or more aspects of the present disclosure may be easily used for developing mobile applications for wearable devices. In addition, since the machine learning model or the deep learning model is easy to relearn, one or more aspects of the present disclosure can realize personalized bladder urine volume estimation. In addition, the urine volume estimation model 1550 can be easily maintained and improved, and can have excellent model expandability and model universality.

Figure 16:
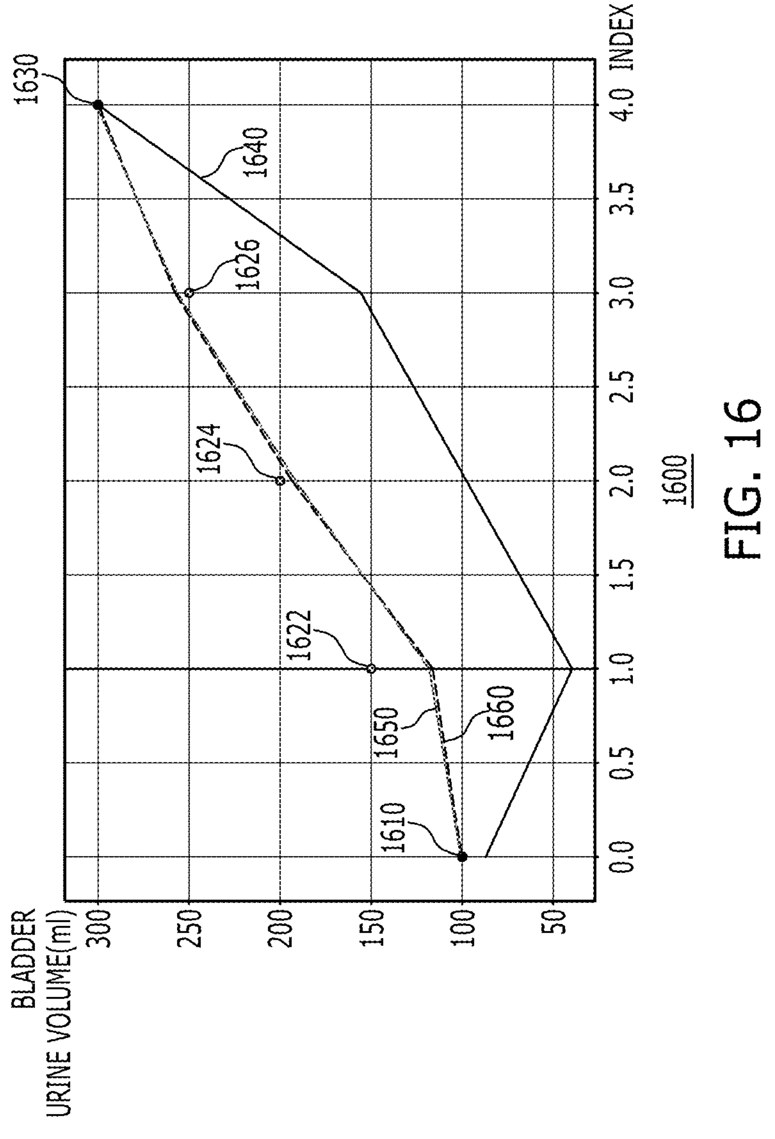
FIG. 16 is a graph illustrating a plurality of examples of a urine volume estimation model according to an aspect of the present disclosure.

FIG. 16 is a graph illustrating a plurality of examples of a urine volume estimation model according to an aspect of the present disclosure. Referring to FIG. 16, a urine volume estimation graph 1600 may display urine volume estimation results of a plurality of urine volume estimation models. Specifically, the urine volume estimation graph 1600 may display a first graph 1640, a second graph 1650, and a third graph 1660. In FIG. 16, the third graph 1660 may be displayed as a dotted line graph. In addition, the urine volume estimation graph 1600 may display a first actual urine volume included in a first learning dataset 1610 and a second actual urine volume included in a second learning dataset 1630. In addition, the urine volume estimation graph 1600 may display a first comparative actual urine volume included in the first comparative dataset 1622, a second comparative actual urine volume included in the second comparative dataset 1624, and a third comparative actual urine volume included in the third comparative dataset 1626. The urine volume estimation graph 1600 may display an index on the x-axis and a bladder urine volume (actual urine volume and/or estimated urine volume) on the y-axis. At this time, the index may be an indicator for indicating the passage of time. For example, the index at the time when the first measurement cycle was performed may be referred to as 0, and the index at the time when the second measurement cycle was performed may be referred to as 4.

In an aspect, the first learning dataset 1610 may include pairs of the first actual urine volume and the first optical characteristic value set. Additionally, the second learning dataset 1630 may include pairs of the second actual urine volume and the second optical characteristic value set. In an aspect, the first comparative dataset 1622 may include pairs of the first comparative actual urine volume and the first comparative optical characteristic value set. Similarly, the second comparative dataset 1624 may include pairs of the second comparative actual urine volume and the second comparative optical characteristic value set, and the third comparative dataset 1626 may include pairs of the third comparative actual urine volume and the third comparative optical characteristic value set. Here, the plurality of learning datasets 1610 and 1630 and the plurality of comparative datasets 1622, 1624, and 1626 may be obtained by performing measurement cycles. For example, the plurality of learning datasets 1610 and 1630 and the plurality of comparative datasets 1622, 1624, and 1626 may be obtained for a specific user wearing a medical device (for example, the medical device 100 described above in FIG. 1) on the skin over the bladder.

In one example, the first actual urine volume may be the actual bladder urine volume of the specific user at the time when the first measurement was performed. In addition, the second actual urine volume may be the actual bladder urine volume of the specific user at the time when the second measurement of the bladder of the specific user was performed. Referring to FIG. 16, the first actual urine volume may be about 100 ml, and the second actual urine volume may be about 300 ml. The method of measuring the actual urine volume may be understood based on the contents described above with reference to FIG. 14.

Similarly, the method of measuring the first to third comparative actual urine volumes may be the same as the method of measuring the first and second actual urine volumes. In this case, the first to third comparative actual urine volumes may be actual urine volumes that are not used for learning the urine volume learning model. In addition, the first to third comparative optical characteristic value sets may be optical characteristic value sets that are not used for learning the urine volume learning model.

In one example, the first to third comparative actual urine volumes may be selected between the first and second actual urine volumes. For example, the first to third comparative actual urine volumes may be selected as values having the same interval between the first and second actual urine volumes. Referring to FIG. 16, if the first actual urine volume is 100 ml and the second actual urine volume is 300 ml, the first comparative actual urine volume may be selected as 150 ml, the second comparative actual urine volume as 200 ml, and the third comparative actual urine volume as 250 ml. In FIG. 16, three comparative actual urine volumes are selected, but more or fewer comparative actual urine volumes may be selected.

In FIG. 16, the "comparative measurement cycle" may represent a measurement cycle for estimating a comparative optical characteristic value set. In this case, the index of the time at which the first comparative measurement cycle was performed may be referred to as 1, the index of the time at which the second comparative measurement cycle was performed may be referred to as 2, and the index of the time at which the third comparative measurement cycle was performed may be referred to as 3. In one example, the n-th comparative measurement cycle may be performed corresponding to the time at which the n-th comparative actual urine volume was measured. In addition, the n-th comparative optical characteristic value set may be estimated based on the n-th comparative optical dataset detected through the n-th comparative measurement cycle.

In an aspect, the first urine volume estimation model may be a model learned from the first learning dataset 1610 and the second learning dataset 1630. For example, the first urine volume estimation model may use an ANN model. The first graph 1640 may display the urine volume estimation result of the first urine volume estimation model. In addition, the teacher model may be a model learned from the first learning dataset 1610 and the second learning dataset 1630. For example, the teacher model may use a Random Forest model or a Linear Regression model. The second graph 1650 may display the urine volume estimation result of the teacher model. In addition, the second urine volume estimation model may be a model learned from the first learning dataset 1610, the second learning dataset 1630, and a plurality of additional learning datasets. At this time, the plurality of additional learning datasets may be generated by the teacher model. For example, the second urine volume estimation model may use an ANN model. The third graph 1660 may display the urine volume estimation result of the second urine volume estimation model.

The urine volume estimation result of the first urine volume estimation model, the urine volume estimation result of the second urine volume estimation model, and the urine volume estimation result of the teacher model may be compared as shown in Table 3 below. Referring to FIG. 16, the urine volume estimation graph 1600 may be shown as shown in Table 3 below.

TABLE 3

| Index | Actual urine volume (including comparative actual urine volume, ml) | Urine volume estimated by teacher model (ml) | Estimation error of teacher model (ml) | Urine volume estimated by first urine volume estimation model (ml) | Estimation error of first urine volume estimation model (ml) | Urine volume estimated by second urine volume estimation model (ml) | Estimation error of second urine volume estimation model (ml) |
|---|---|---|---|---|---|---|---|
| 0 | 100 | 100.0 | 0.0 | 86.3 | 13.7 | 99.8 | 0.2 |
| 1 | 150 | 117.6 | 32.4 | 39.1 | 110.9 | 115.6 | 34.4 |
| 2 | 200 | 190.9 | 9.1 | 98.9 | 101.1 | 192.5 | 7.5 |
| 3 | 250 | 255.7 | 5.7 | 155.3 | 94.7 | 256.6 | 6.6 |
| 4 | 300 | 300.0 | 0.0 | 300.0 | 0.0 | 298.8 | 1.2 |

In Table 3, the urine volume estimation model may include the first urine volume estimation model, the second urine volume estimation model, and the teacher model. The urine volume estimation model may estimate the urine volume by receiving an optical characteristic value set (or a comparative optical characteristic value set) corresponding to each index. For example, the first urine volume estimation model may generate a urine volume estimation result corresponding to about 39.1 ml by receiving the first comparative optical characteristic value set. At this time, the estimation error of the first urine volume estimation model may be 110.9 ml obtained by subtracting 39.1 ml, which is the estimation result of the first urine volume estimation model, from 150 ml, which is the first comparative actual urine volume. Similarly, the second urine volume estimation model may generate a urine volume estimation result corresponding to about 115.6 ml by receiving the first comparative optical characteristic value set. At this time, the estimation error of the second urine volume estimation model may be 34.4 machine learning obtained by subtracting 115.6 ml, which is the estimation result of the first urine volume estimation model, from 150 ml, which is the first comparative actual urine volume. It may be confirmed through Table 3 or the urine volume estimation graph 1600 that the second urine volume estimation model, which has learned a plurality of learning datasets and a plurality of additional learning datasets, has a smaller urine volume estimation error than the first urine volume estimation model, which has learned a plurality of learning datasets.

If the amount of the learning dataset is not large, data augmentation may be performed by generating a plurality of additional learning datasets through the teacher model. Since the urine volume prediction model learns more data through data augmentation, a method of predicting the bladder urine volume, which is designed based on medical knowledge and diagnosis, may be implemented.

Figure 17:
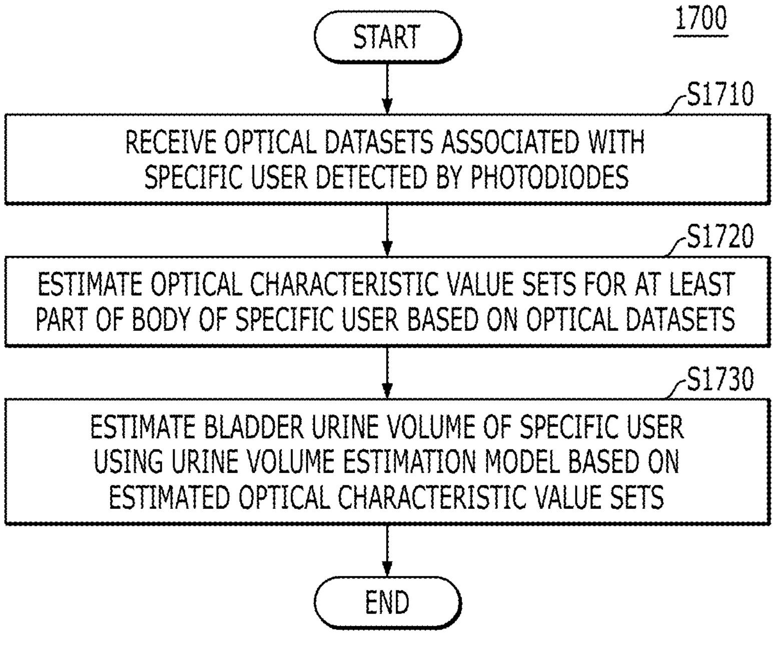
FIG. 17 is a flowchart for explaining a bladder urine volume prediction method according to an aspect of the present disclosure.

FIG. 17 is a flowchart for explaining a bladder urine volume prediction method 1700 according to an aspect of the present disclosure. The method 1700 may be performed by a control unit (or at least one processor) of a medical device, a user terminal, and/or at least one processor of an information processing system. The method 1700 may begin with a step S2010 in which the processor receives an optical dataset associated with a specific user detected by a plurality of photodiodes. In an aspect, the processor may estimate an optical characteristic value set for at least a part of the body of the specific user based on the optical dataset In an aspect, the processor estimates a bladder urine volume of the specific user using a urine volume estimation model based on the estimated optical characteristic value set. The urine volume estimation model may be a deep learning-based model or a machine learning-based model that has learned a plurality of learning datasets. In this case, the plurality of learning datasets may include pairs of actual urine volumes of the specific user and optical characteristic value sets associated with the actual urine volumes.

In an aspect, the plurality of learning datasets may include a first learning dataset and a second learning dataset. The first learning dataset may include a pair of a first actual urine volume of the specific user and a first learning optical characteristic value set associated with the first actual urine volume. In addition, the second learning dataset may include a pair of a second actual urine volume of the specific user and a second learning optical characteristic value set associated with the second actual urine volume. In the case, the second actual urine volume may be greater than the first actual urine volume. For example, the first actual urine volume may correspond to a minimum bladder urine capacity of the specific user, and the second actual urine volume may correspond to the maximum bladder urine capacity of the specific user.

In an aspect, a teacher model may be generated by learning the plurality of learning datasets. In addition, the urine volume estimation model may further learn a single or a plurality of additional learning datasets. In this case, the additional learning datasets may include a pair of an additional learning urine volume and an additional learning optical characteristic value set estimated by inputting the additional learning urine volume into the teacher model, and the additional learning urine volume may be greater than the first urine volume and smaller than the second urine volume. In addition, the urine volume estimation model may be learned by applying a predetermined weight to the plurality of learning datasets.

In an aspect, the processor receives obesity information associated with the specific user. In this case, the urine volume estimation model may further learn learning obesity information. After that, the processor estimates the urine volume using the urine volume estimation model based on the received obesity information and the optical characteristic value set.

The above flowchart and the above description are exemplary only, and may be implemented differently in some embodiments. For example, in some embodiments, the order of each step may be reversed, some steps may be performed repeatedly, some steps may be omitted, and some steps may be added.

The method described above may be provided as a computer program stored in a computer-readable recording medium for execution on a computer. The medium may be a type of medium that continuously stores a program executable by a computer, or temporarily stores the program for execution or download. In addition, the medium may be a variety of writing means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, and the like. In addition, other examples of the medium may include an application store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies according to design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, and the like. The instructions may be executable by one or more processors, and may cause the processor(s) to perform certain aspects of the functions described in the present disclosure.

If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that may be accessed by a general purpose or special purpose computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code means in the form of instructions or data structures and that may be accessed by a general-purpose or special-purpose computer, or a general-purpose or special-purpose processor. Also, any connection is properly termed a computer-readable medium.

For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor may read information from, and/or write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in a plurality of processing chips or apparatus, and storage may be similarly influenced across a plurality of apparatus. Such apparatus may include PCs, network servers, and portable apparatus.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A bladder urine volume prediction method, performed by at least one processor, the method comprising:

receiving an optical dataset associated with a specific user detected by a plurality of photodiodes, wherein the plurality of photodiodes are configured to detect an intensity of light associated with light irradiated to skin located above a bladder of the specific user, and wherein the plurality of photodiodes comprise a first photodiode, a second photodiode, and a third photodiode;

estimating, based on the optical dataset, an optical characteristic value set for at least a part of a body of the specific user by:

calibrating, using calibration parameters associated with the plurality of photodiodes, the optical dataset;

calculating, based on the calibrated optical dataset, a normalized diffuse reflectance of the second photodiode relative to the first photodiode;

calculating, based on the calibrated optical dataset, a normalized diffuse reflectance of the third photodiode relative to the first photodiode; and estimating the optical characteristic value set based on:

the normalized diffuse reflectance of the second photodiode relative to the first photodiode, and the normalized diffuse reflectance of the third photodiode relative to the first photodiode;

estimating, using a urine volume estimation model based on the estimated optical characteristic value set, a bladder urine volume of the specific user; and outputting, based on the estimated bladder urine volume of the specific user, a signal indicating the estimated bladder urine volume of the specific user.

2. The bladder urine volume prediction method according to claim 1, wherein:

the urine volume estimation model is a deep learning-based model or a machine learning-based model that has learned a plurality of learning datasets, and the plurality of learning datasets comprise pairs of actual urine volumes of the specific user and optical characteristic value sets associated with the actual urine volumes.

3. The bladder urine volume prediction method according to claim 2, wherein:

the plurality of learning datasets comprise a first learning dataset and a second learning dataset, the first learning dataset comprises a pair of a first actual urine volume of the specific user and a first learning optical characteristic value set associated with the first actual urine volume, the second learning dataset comprises a pair of a second actual urine volume of the specific user and a second learning optical characteristic value set associated with the second actual urine volume, and the second actual urine volume is greater than the first actual urine volume.

4. The bladder urine volume prediction method according to claim 3, wherein:

a teacher model is generated by learning the plurality of learning datasets, the urine volume estimation model is configured to further learn at least one additional learning dataset, the at least one additional learning dataset comprises a pair of an additional learning urine volume and an additional learning optical characteristic value set estimated by inputting the additional learning urine volume into the teacher model, and the additional learning urine volume is greater than the first actual urine volume and smaller than the actual second urine volume.

5. The bladder urine volume prediction method according to claim 4, wherein the urine volume estimation model is learned by applying a predetermined weight to the plurality of learning datasets.

6. The bladder urine volume prediction method according to claim 3, wherein the first actual urine volume corresponds to a minimum bladder urine capacity of the specific user, and the second actual urine volume corresponds to a maximum bladder urine capacity of the specific user.

7. The bladder urine volume prediction method according to claim 1, further comprising:

outputting, based on the estimated bladder urine volume being greater than a predetermined reference value, a message recommending voiding.

8. The bladder urine volume prediction method according to claim 2, wherein:

the urine volume estimation model is configured to further learn learning obesity information, and the method further comprises:

receiving obesity information associated with the specific user, and the estimating of the urine volume comprises:

estimating, using the urine volume estimation model based on the received obesity information and the optical characteristic value set, the urine volume.

9. A non-transitory computer-readable medium storing instructions that, when executed, cause a computing device to:

receive an optical dataset associated with a specific user detected by a plurality of photodiodes, wherein the plurality of photodiodes are configured to detect an intensity of light associated with light irradiated to skin located above a bladder of the specific user, and wherein the plurality of photodiodes comprise a first photodiode, a second photodiode, and a third photodiode;

estimate, based on the optical dataset, an optical characteristic value set for at least a part of a body of the specific user by:

calibrating, using calibration parameters associated with the plurality of photodiodes, the optical dataset;

calculating, based on the calibrated optical dataset, a normalized diffuse reflectance of the second photodiode relative to the first photodiode;

calculating, based on the calibrated optical dataset, a normalized diffuse reflectance of the third photodiode relative to the first photodiode; and estimating the optical characteristic value set based on:

the normalized diffuse reflectance of the second photodiode relative to the first photodiode, and the normalized diffuse reflectance of the second photodiode relative to the first photodiode;

estimate, using a urine volume estimation model based on the estimated optical characteristic value set, a bladder urine volume of the specific user; and output, based on the estimated bladder urine volume of the specific user, a signal indicating the estimated bladder urine volume of the specific user.

10. A user terminal comprising:

a communication interface;

at least one processor; and a memory storing instructions that, when executed by the at least one processor, cause the user terminal to:

receive an optical dataset associated with a specific user detected by a plurality of photodiodes, wherein the plurality of photodiodes are configured to detect an intensity of light associated with light irradiated to skin located above a bladder of the specific user, and wherein the plurality of photodiodes comprise a first photodiode, a second photodiode, and a third photodiode;

estimate, based on the optical dataset, an optical characteristic value set for at least a part of a body of the specific user by:

calibrating, using calibration parameters associated with the plurality of photodiodes, the optical dataset;

calculating, based on the calibrated optical dataset, a normalized diffuse reflectance of the second photodiode relative to the first photodiode;

calculating, based on the calibrated optical dataset, a normalized diffuse reflectance of the third photodiode relative to the first photodiode; and estimating the optical characteristic value set based on:

the normalized diffuse reflectance of the second photodiode relative to the first photodiode, and the normalized diffuse reflectance of the third photodiode relative to the first photodiode;

estimate, using a urine volume estimation model based on the estimated optical characteristic value set, a bladder urine volume of the specific user; and output, based on the estimated bladder urine volume of the specific user, a signal indicating the estimated bladder urine volume of the specific user.

11. The non-transitory computer-readable medium of claim 9, wherein:

the urine volume estimation model is a deep learning-based model or a machine learning-based model that has learned a plurality of learning datasets, and the plurality of learning datasets comprise pairs of actual urine volumes of the specific user and optical characteristic value sets associated with the actual urine volumes.

12. The non-transitory computer-readable medium of claim 11, wherein:

the plurality of learning datasets comprise a first learning dataset and a second learning dataset, the first learning dataset comprises a pair of a first actual urine volume of the specific user and a first learning optical characteristic value set associated with the first actual urine volume, the second learning dataset comprises a pair of a second actual urine volume of the specific user and a second learning optical characteristic value set associated with the second actual urine volume, and the second actual urine volume is greater than the first actual urine volume.

13. The non-transitory computer-readable medium of claim 12, wherein:

a teacher model is generated by learning the plurality of learning datasets, the urine volume estimation model is configured to further learn at least one additional learning dataset, the at least one additional learning dataset comprises a pair of an additional learning urine volume and an additional learning optical characteristic value set estimated by inputting the additional learning urine volume into the teacher model, and the additional learning urine volume is greater than the first actual urine volume and smaller than the actual second urine volume.

14. The non-transitory computer-readable medium of claim 13, wherein the urine volume estimation model is learned by applying a predetermined weight to the plurality of learning datasets.

15. The non-transitory computer-readable medium of claim 12, wherein the first actual urine volume corresponds to a minimum bladder urine capacity of the specific user, and the second actual urine volume corresponds to a maximum bladder urine capacity of the specific user.

16. The user terminal of claim 10, wherein:

the urine volume estimation model is a deep learning-based model or a machine learning-based model that has learned a plurality of learning datasets, and the plurality of learning datasets comprise pairs of actual urine volumes of the specific user and optical characteristic value sets associated with the actual urine volumes.

17. The user terminal of claim 16, wherein:

the plurality of learning datasets comprise a first learning dataset and a second learning dataset, the first learning dataset comprises a pair of a first actual urine volume of the specific user and a first learning optical characteristic value set associated with the first actual urine volume, the second learning dataset comprises a pair of a second actual urine volume of the specific user and a second learning optical characteristic value set associated with the second actual urine volume, and the second actual urine volume is greater than the first actual urine volume.

18. The user terminal of claim 17, wherein:

a teacher model is generated by learning the plurality of learning datasets, the urine volume estimation model is configured to further learn at least one additional learning dataset, the at least one additional learning dataset comprises a pair of an additional learning urine volume and an additional learning optical characteristic value set estimated by inputting the additional learning urine volume into the teacher model, and the additional learning urine volume is greater than the first actual urine volume and smaller than the actual second urine volume.

19. The user terminal of claim 18, wherein the urine volume estimation model is learned by applying a predetermined weight to the plurality of learning datasets.

20. The user terminal of claim 17, wherein the first actual urine volume corresponds to a minimum bladder urine capacity of the specific user, and the second actual urine volume corresponds to a maximum bladder urine capacity of the specific user.

* * * * *